US009662515B2

(12) United States Patent
Köhler et al.

(10) Patent No.: US 9,662,515 B2
(45) Date of Patent: May 30, 2017

(54) METHOD FOR PRODUCING 4-AMINOBUTYRIC ACID FROM ALGAE

(75) Inventors: Tim Köhler, Dorsten (DE); Jennifer Schild, Solingen (DE); Matthias Mentel, Dortmund (DE); Peter Lersch, Dinslaken (DE); Mike Farwick, Essen (DE); Christian Weitemeyer, Seeburg (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 14/239,398

(22) PCT Filed: Jul. 20, 2012

(86) PCT No.: PCT/EP2012/064261
§ 371 (c)(1),
(2), (4) Date: May 30, 2014

(87) PCT Pub. No.: WO2013/023873
PCT Pub. Date: Feb. 21, 2013

(65) Prior Publication Data
US 2014/0308310 A1    Oct. 16, 2014

(30) Foreign Application Priority Data

Aug. 18, 2011 (DE) .......................... 10 2011 110 996

(51) Int. Cl.
| A61Q 19/00 | (2006.01) |
| A61K 8/44 | (2006.01) |
| C12P 13/00 | (2006.01) |
| A61Q 5/00 | (2006.01) |
| A61K 8/99 | (2017.01) |
| A61Q 5/12 | (2006.01) |
| A61Q 17/04 | (2006.01) |
| A61Q 19/06 | (2006.01) |
| A61Q 19/08 | (2006.01) |
| A61K 36/04 | (2006.01) |
| A61Q 5/02 | (2006.01) |

(52) U.S. Cl.
CPC ............. *A61Q 19/007* (2013.01); *A61K 8/44* (2013.01); *A61K 8/99* (2013.01); *A61K 36/04* (2013.01); *A61Q 5/00* (2013.01); *A61Q 5/12* (2013.01); *A61Q 17/04* (2013.01); *A61Q 19/002* (2013.01); *A61Q 19/004* (2013.01); *A61Q 19/06* (2013.01); *A61Q 19/08* (2013.01); *C12P 13/005* (2013.01); *A61Q 5/02* (2013.01)

(58) Field of Classification Search
None
See application file for complete search history.

(56) References Cited

U.S. PATENT DOCUMENTS

| 5,536,654 A * | 7/1996 | Gudin ...................... C12R 1/89 435/189 |
| 2006/0018867 A1* | 1/2006 | Kawasaki .............. A61K 8/898 424/70.122 |
| 2006/0198809 A1 | 9/2006 | Herrel |
| 2008/0299147 A1 | 12/2008 | Dillon et al. |
| 2009/0069213 A1 | 3/2009 | Avila et al. |
| 2010/0170144 A1* | 7/2010 | Day ..................... C12P 7/6418 44/388 |
| 2012/0107919 A1 | 5/2012 | Broneske et al. |

FOREIGN PATENT DOCUMENTS

| CN | 101555501 A | 10/2009 |
| CN | 101838672 A | 9/2010 |
| DE | 4411486 C1 | 3/1995 |
| DE | 29607285 U1 | 8/1996 |
| DE | 10136645 A1 | 2/2003 |
| DE | 102008001788 A1 | 11/2009 |
| DE | 102009028474 A1 | 2/2011 |
| EP | 1277831 A2 | 1/2003 |
| JP | 2-154681 | 6/1990 |
| WO | WO9105849 | 5/1991 |
| WO | WO2007007989 | 1/2007 |
| WO | WO2008081095 | 10/2008 |
| WO | WO2010149154 A2 | 12/2010 |
| WO | WO2011018082 | 2/2011 |

OTHER PUBLICATIONS

Anderson et a. Algal Culturing Techniques. Academic Press, 2005, p. 433.*
Allen et al. Archiv fur Mikrobiologie, Bd. 32, S. 270-277, 1959.*
Beale, S.I., et al., "Biosynthesis of Phycobilins", The Journal of Biological Chemistry, Nov. 25, 1991, pp. 22328-22332, vol. 266, No. 33.
Ito, K. et al., "GABA-synthesizing enzyme, GAD67, from dermal fibroblasts: Evidence for a new skin function", Biochimica et Biophysica, Dec. 29, 2006, pp. 291-296, vol. 1770, No. 2.
Chinese Office Action, with English-language translation thereof, dated Apr. 29, 2015 received in a corresponding foreign application.
Morse, A.N.C. and Morse, D.E., "GABA-mimetic molecules from Porphyra (Rhodophyta) induce metamorphosis of Haliotis (Gastropoda) larvae", Hydrobiologia, 1984, 116-117 (1): 155-158.
Carmona, E., et al., "Purification of GABA on Small Columns of Dowex 50 W; Combination with a Method of Separation of Biogenic Amines", Acta Pharmacol, et Toxicol, Mar. 1980, 46(3): 235-40.

(Continued)

*Primary Examiner* — Oluwatosin Ogunbiyi
(74) *Attorney, Agent, or Firm* — Scully Scott Murphy and Presser; Frank Digiglio

(57) ABSTRACT

The invention relates to a process for the production of 4-aminobutyric acid, also referred to as gamma-aminobutyric acid, in short GABA, to a process for the production of an extract comprising 4-aminobutyric acid, to a process for the preparation of a cosmetic formulation comprising 4-aminobutyric acid, and to the use of *Cyanidium caldarium* cells or cell components in cosmetic applications.

5 Claims, 16 Drawing Sheets

(56) References Cited

OTHER PUBLICATIONS

Figure 1:
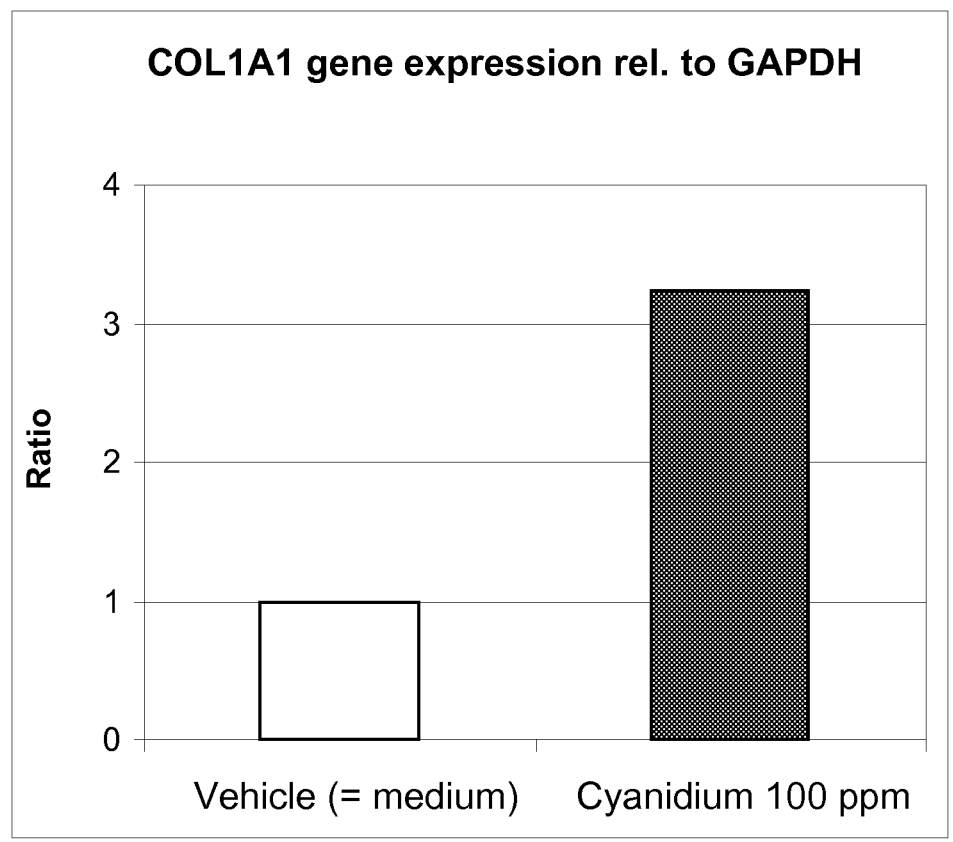

Livak, K.J. and Schmittgen, T.D., Analysis of Relative Gene Expression Data using Real Time Quantitative PCR and the 2 (-delta delta C(T)) Method. Methods, 2001, 25: 402-408.

"A place in the sun", Flanders Today, http://www.flanderstoday.eu/current-affairs/place-sun, accessed Dec. 26, 2015, 6 pages.

Beale, S. I., et al., "N-Methyl Mesoporphyrin IX Inhibits Phycocyanin, but Not Chlorophyll Synthesis in Cyanidium caldarium" Plant Physoil. 71:263-268 (1983).

* cited by examiner

METHOD FOR PRODUCING 4-AMINOBUTYRIC ACID FROM ALGAE

FIELD OF THE INVENTION

The invention relates to a process for the production of 4-aminobutyric acid, also referred to as gamma-aminobutyric acid, in short GABA, to a process for the production of an extract comprising 4-aminobutyric acid, to a process for the preparation of a cosmetic formulation comprising 4-aminobutyric acid, and to the use of *Cyanidium caldarium* cells or cell components in cosmetic applications.

INCORPORATION BY REFERENCE OF SEQUENCE LISTING

The Sequence Listing in an ASCII text file, named 30762_SequenceListing3_ST25.txt of 9 KB, created on Dec. 28, 2015, and submitted to the United States Patent and Trademark Office via EFS-Web, is incorporated herein by reference.

PRIOR ART

The positive effects of GABA on the skin were first described by Ito et al. in Biochim Biophys Acta. 2007 February; 1770(2):291-6 when the expression of GAD67, which has otherwise only been described as being neuronally localized and which catalyses GABA synthesis, has been demonstrated in human dermal fibroblasts.

It has been demonstrated that GABA is capable of upregulating hyaluronic acid synthesis in fibroblasts and that GAD67 has a positive effect on collagen synthesis. Cosmetics comprising GABA (INCI: aminobutyric acid) are found in the fields of decorative cosmetics, deodorants, wet wipes, skincare and shower products. Here, GABA is described as being a skin-identical substance with a muscle-relaxing activity, skin-lightening activity, moisturizing activity and as a substance with a stimulating activity on collagen and matrikin synthesis. Fields of application are uses such as anti-ageing, anti-wrinkle, tightening and smoothing lip lines, reducing expression lines, reducing thin lines and crow's feet. The origin of the GABA used is the microbial fermentation of plants. Here, for example, rice germ is fermented for several years at 37° C.

To date, the synthesis of GABA has been described occurring almost without exception in higher organisms only.

In algae, only the occurrence of GABA mimetics in, for example, Porphyrahas been described to date byMorse and Morse in Hydrobiologia, 116-117 (1): 155-158.

It was an object of the invention to provide a cosmetic formulation which comprises GABA, where the GABA source is based on rapidly growing microorganisms which can be cultured readily.

DESCRIPTION OF THE INVENTION

Surprisingly, it has been found that the alga *Cyanidium caldarium* comprises large amounts of GABA and that it can be used outstandingly for producing GABA and also for producing a cosmetic.

This is surprising in particular because it has previously been considered impossible to find an alga which is capable of synthesising GABA.

Subject matter of the present invention are therefore a process for the production of GABA and of a GABA-containing cosmetic using *Cyanidium caldarium* cells.

A further subject matter of the invention is the cosmetic obtainable by the process described, and the use of *Cyanidium caldarium* cells or cell components in a cosmetic formulation.

An advantage of the present invention is the sustainability owing to the use of a renewable raw material.

A further advantage is the simple provision of the GABA owing to the fact that the *Cyanidium caldarium* cells can be processed readily.

Yet another advantage of the present invention is that *Cyanidium caldarium* cells do not comprise any secondary components which interfere with a cosmetic.

Yet another advantage of the present invention is that *Cyanidium caldarium* cells comprise further secondary components which are advantageous for a cosmetic, such as, for example, nutrients, minerals, nonessential and essential amino acids, ornithine and polyphenols.

Yet another advantage of the present invention is that the cosmetic according to the invention is capable of upregulating marker genes of the extracellular matrix.

In particular fibrillin and elastin, the most important structural components of elastic fibres, are advantageously upregulated in a uniform manner.

Yet another advantage is that the cosmetic according to the invention has an antioxidative activity and a nutritive effect on the skin.

Yet another advantage is that the cosmetic according to the invention proves to be effective for a wide range of skin types, especially for aged skin, and has anti-inflammatory and skin-calming activity.

The subject matter of the present invention, therefore, is a process for the production of 4-aminobutyric acid, comprising the process steps A) culturing *Cyanidium caldarium* cells in an aqueous medium,
B) disrupting the *Cyanidium caldarium* cells, if appropriate
C) removing the solid cell components to obtain an extract and, if appropriate,
D) further purifying the 4-aminobutyric acid.

In the context of the present invention, the expression "*Cyanidium caldarium*" is to be understood as meaning the alga classified as *Cyanidium caldarium* (Tilden) Geitler from the family Cyanidiaceae.

The expression "aqueous" is understood as meaning a water content of at least 50% by weight based on the total composition to which "aqueous" refers, in the present case specifically the medium.

The expression "disrupting the cells" is understood as meaning the destroying of the cell membrane, in particular of the external cell membrane.

The expression "extract" is understood as meaning liquid mixture compositions of various components, it being possible for these mixture compositions to be isolated from the *Cyanidium caldarium* cells.

The expression "cell components" is understood as meaning mixture compositions of various components which can be isolated from *Cyanidium caldarium* cells.

All the percentages indicated (%) are percent by weight unless otherwise specified.

*Cyanidium caldarium* cells which are preferred in accordance with the invention are cells of strain SAG 16.91.

It is preferred in accordance with the invention that the *Cyanidium caldarium* cells are, in process step A), cultured at an elevated temperature, therefore in a preferred temperature range of from 20° C. to 60° C., in particular of from 35° C. to 45° C. It is preferred that the culturing at elevated temperature is done over a period of from 7 days to 192 days, in particular from 28 days to 56 days. This makes it possible to provide an extract or a cosmetic which, besides GABA, comprises polyamines such as, for example, spermine, spermidine and norspermine.

The aqueous medium in process step A) preferably has a pH at 25° C. of from 1.5 to 6, preferably of from 2 to 3.

Disrupting the cells in process step B) can be done by sonicating a suspension of the algae culture, by applying an osmotic shock, by high-pressure homogenization (for example French press, Manton-Gaulin homogenizer), by hot-water extraction, by employing high shear forces (for example Ultra-Turrax, Potter-Elvehjem method), by wet-grinding in stirred-ball mills, by letting down the pressure, with the aid of enzymes such as, for example, polysaccharidases such as glucanase, hemicellulase, cellulase or else commercial enzymes such as SP-311 (novo) or by any desired combinations of these abovementioned methods.

In process step B) the cells are preferably disrupted in an aqueous medium so as to preferably obtain an aqueous extract. Especially preferably, the aqueous medium of process step B) corresponds to the medium of process step A), in particular it takes the form of the same medium.

Especially preferred in process step B) is the disruption by hot water in combination with an enzymatic cell disruption.

The removing of the solid cell components in process step C) may be done for example by centrifugation, sedimentation or filtration.

The further purification of the GABA can be done for example as described in Carmona et al., Acta Pharmacol Toxicol (Copenh). 1980 March; 46(3):235-40.

A further subject matter of the present invention is also a process for the production of an extract comprising 4-aminobutyric acid, comprising the process steps
A) culturing *Cyanidium caldarium* cells in an aqueous medium,
B) disrupting the *Cyanidium caldarium* cells, if appropriate
C) removing the solid cell components to obtain an extract, with process steps A) to C) corresponding to the first-mentioned process of the present invention and corresponding preferred embodiments likewise being preferred. Preferably, the process according to the invention for the production of an extract is composed of steps A), B) and C).

Therefore, an extract obtainable by the abovementioned process, too, is part of the present invention.

The extract is preferably an aqueous extract.

Extracts which are preferred in accordance with the invention are characterized in that they comprise, as additional component, polyamines such as, for example, spermine, spermidine and norspermine.

Since the extract can advantageously be employed for the preparation of cosmetic formulations, it is preferred to provide the extract with preservatives. In this context, the preferred preservative is selected from among benzoate and sorbate.

A preferred extract according to the invention is characterized in that it comprises from 0.01% by weight to 10% by weight, preferably from 0.5% by weight to 5% by weight and especially preferably from 1% by weight to 3% by weight of dry matter of *Cyanidium caldarium* cell components, where the percentage by weight is based on the total extract.

A preferred extract according to the invention is characterized in that it comprises from 0.01% by weight to 7% by weight, preferably from 0.25% by weight to 3% by weight and especially preferably from 0.5% by weight to 1.5% by weight of preservative, where the percentage by weight is based on the total extract.

A further subject matter of the present invention is also a process for the preparation of a cosmetic formulation comprising 4-aminobutyric acid, comprising the process steps
A) culturing *Cyanidium caldarium* cells in an aqueous medium,
B) disrupting the *Cyanidium caldarium* cells, if appropriate
C) removing the solid cell components to obtain an extract and
E) incorporating the disrupted *Cyanidium caldarium* cells from process step B) and/or the extract from process step C) into a cosmetic formulation,
with process steps A) to C) corresponding to the first-mentioned process of the present invention and corresponding preferred embodiments likewise being preferred. Preferably, the process according to the invention for the preparation of a cosmetic formulation is composed of process steps A), B), C) and E).

Preferably, only the extract from process step C) is incorporated in process step E).

A further subject matter of the present invention is a cosmetic formulation comprising GABA obtainable by the process according to the invention, and a cosmetic formulation comprising GABA and *Cyanidium caldarium* cells and/or cell components, and a cosmetic formulation comprising the extract according to the invention.

The formulation according to the invention may take the form of any cosmetic formulation, in particular skin formulations, nail formulations and hair formulations, with skin formulations being especially preferred.

The characteristic properties of *Cyanidium caldarium* cells and/or cell components such as, for example, the moderate tendency to form residues on and in the skin and/or hair, have a promoting effect on the structure of the skin and/or the hair, thus increasing the stability, resistance, colour intensity and strength, in particular tensile strength, especially of the hair.

The hair formulation according to the invention is not limited to leave-on applications (hair conditioner, hair treatment). The hair formulation according to the invention is advantageously also presented in the form of rinse-off products (for example shampoos, skin-cleansing products).

Formulations which are suitable for the use on the skin and which are preferred in accordance with the invention comprise in particular: after-shave lotions, face care products for men, sunscreens, after-sun products, lip care products, anti-wrinkle care products, products which strengthen the skin barrier, anti-ageing products, décolletage products, anti-cellulite products, contouring products, moisturizing products, products which protect from harmful environmental influences, skin-calming products and skin-irritation-reducing products.

Formulations according to the invention may be employed for example in the form of an emulsion, a suspension, a solution, a cream, an ointment, a paste, a gel, an oil, a powder, an aerosol, a stick, a spray or a foam.

The cosmetic formulation according to the invention may comprise for example at least one additional component selected from the group of the
    emollients,
    emulsifiers,
    thickeners/viscosity regulators/stabilizers,
    antioxidants,
    hydrotropes (or polyols),
    solids and fillers, pearl lustre additives,
deodorant and antiperspirant active substances,
insect repellents,
self-tanning agents,
preservatives,
conditioners,
perfumes,
colorants,
cosmetic active substances,
care additives,
superfatting agents,
solvents,
UV filters.

Substances which can be employed as examples of representatives of the individual groups are known to a person skilled in the art and can be found for example in the German application DE 102008001788.4. This patent application is herewith incorporated by way of reference and therefore forms part of the disclosure.

As regards further optional components and the amounts in which these components are employed, express reference is made to the specialist handbooks known to the skilled worker, for example K. Schrader, "Grundlagen and Rezepturen der Kosmetika", 2nd Edition, page 329 to 341, Hüthig Buch Verlag Heidelberg.

The amounts of the respective additives depend on the intended use.

Typical framework formulas for the respective uses are known prior art and can be found for example in the brochures of the manufacturers of the respective excipients and active substances. As a rule, these existing formulations can be used without implementing changes. If required, however, the desired modifications can be implemented in a problem-free manner by simple experiments to adapt and optimize the formulations.

Cosmetic formulations which are preferred in accordance with the invention are characterized in that they comprise, as additional component, polyamines such as, for example, spermine, spermidine and norspermine and/or a preservative. In this context, the preferred preservative is selected from among benzoate and sorbate.

A preferred cosmetic formulation according to the invention is characterized in that it comprises from 0.00125-1.5 percent by weight, preferably from 0.0025 to 0.625 percent by weight and especially preferably from 0.0125 to 0.0625 percent by weight of dry matter of *Cyanidium caldarium* cells and/or cell components, where the percentage by weight refers to the total formulation.

The cosmetic formulation according to the invention has a high anti-inflammatory activity; therefore, a further subject matter of the present invention is a cosmetic formulation according to the invention against inflammations, in particular against inflammations of the skin, such as, for example, acne.

A further subject matter of the present invention is the use of *Cyanidium caldarium* cells or cell components and of the extract according to the invention in a cosmetic formulation.

The cosmetic formulation according to the invention proves to be effective for a very wide range of skin types, especially for aged skin (chronologically aged skin, photoaged skin, sagging skin, flaccid skin).

The use of the cosmetic formulation according to the invention generally leads to an improved skin structure, whereby the cosmetic formulation according to the invention becomes useful as a universal anti-ageing active substance. In particular, the cosmetic formulation according to the invention can be used for shaping cosmetic treatments, such as, for example, on the chin, the chest, the buttocks and the tummy.

Further positive effects of the cosmetic formulation according to the invention comprise, inter alia, a reduced roughness of the skin, a reduced scaliness of the skin, reduced wrinkle depth and an enhanced skin elasticity, skin firmness and skin thickness.

The topical application, on the skin, of the cosmetic formulation according to the invention leads to a reduction in the signs of stressed, irritated, reddened and inflamed skin. This makes the cosmetic formulation according to the invention particularly suitable for cosmetic products for calming irritated skin, sensitive skin. The anti-inflammatory and skin-calming activity of the cosmetic formulation according to the invention also favours a use for skin-calming after-shave lotions.

The cosmetic formulation according to the invention has a protective activity from harmful intrinsic and extrinsic factors (adverse influences of the environment), whereby damage to cellular macromolecules and to the epidermal lipid barrier can be prevented.

A skin-calming activity of the cosmetic formulation according to the invention can also be observed on reddened skin, which shows sunburn or erythema symptoms due to the sun's radiation. In this respect, the cosmetic formulation according to the invention can also be employed as an active substance for sun protection and after-sun products.

Besides, the cosmetic formulation according to the invention is suitable for the care and protection of the skin, in particular of skin whose epidermal barrier function is reduced as the consequence of certain skin diseases and whose transepidermal water loss is, as a consequence, increased and/or whose skin hydration is reduced. Such skin diseases comprise, inter alia, xerosis, atopic dermatitis, contact dermatitis, psoriasis, ichthyosis, acanthosis, dandruff, photodermatitis, erythema, and keratinisation damage and/or defects. The cosmetic formulation according to the invention is also suitable for use on the skin for alleviating certain effects, such as dry, itchy and flaky skin, which occur for example as the consequence of autoimmune diseases (for example psoriasis).

In the examples mentioned hereinbelow, the present invention is described by way of example; however, it is not intended to limit the invention, whose scope can be seen from all of the description and the claims, to the embodiments mentioned in the examples.

The following figures are part of the examples:

FIG. 1: Expression of the COL1A1 gene in human dermal fibroblasts 24 h after the application of 100 ppm (=100 µg/ml) *Cyanidium caldarium* extract (concentration based on extract dry matter) or pure medium (vehicle) relative to the GAPDHgene expression.

Figure 2:
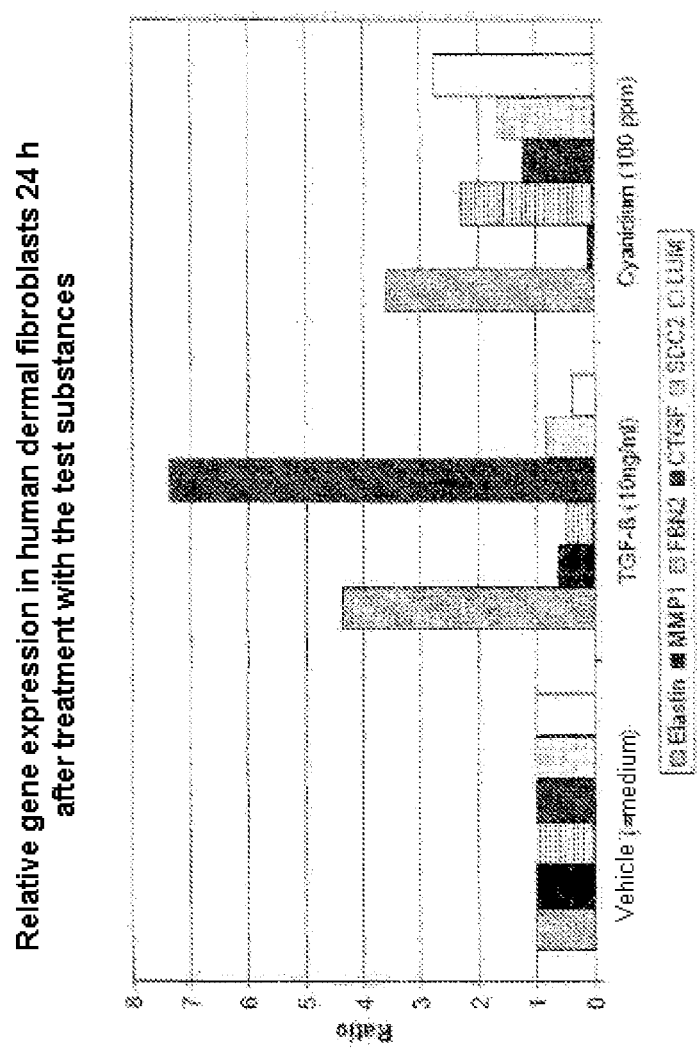

FIG. 2: Expression of various genes in human dermal fibroblasts 24 h after the application of pure medium (vehicle), TGF-β (10 ng/ml, positive control) or 100 ppm (=100 µg/ml) *Cyanidium caldarium* extract (concentration based on extract dry matter) relative to the GAPDH gene expression.

Figure 3:
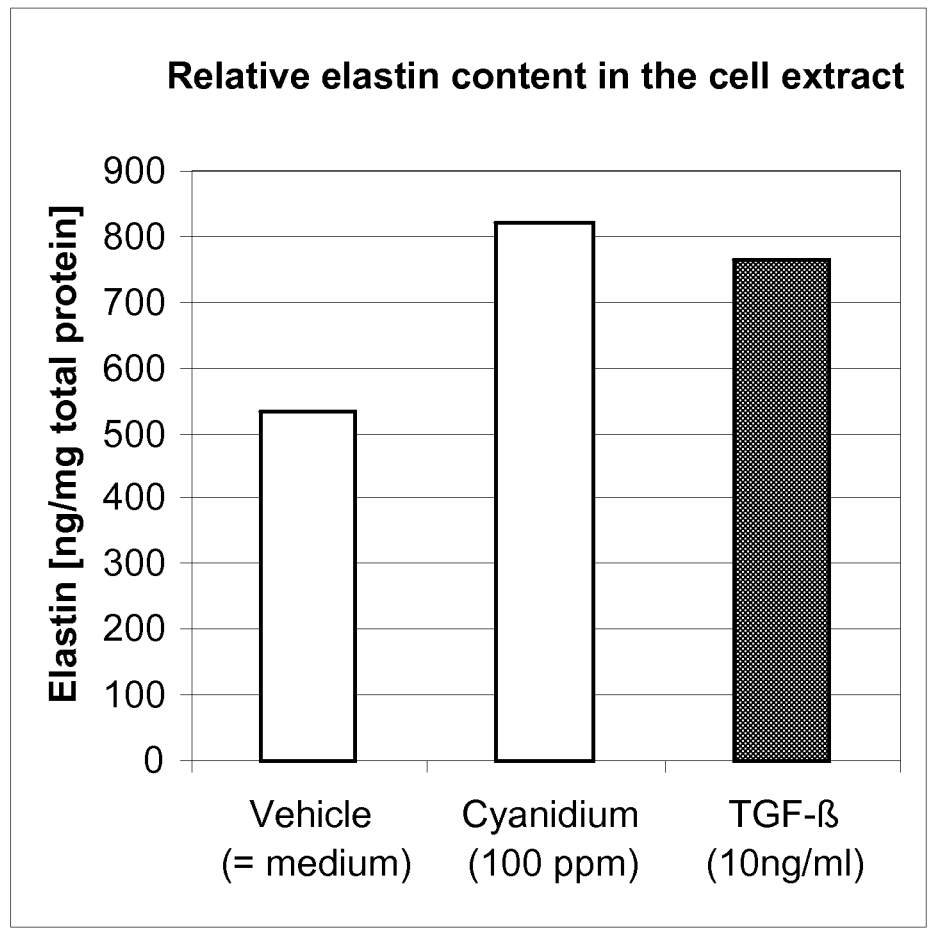

FIG. 3: Elastin protein content in human dermal fibroblasts 24 h after the application of pure medium (vehicle), 100 ppm (=100 µg/ml) *Cyanidium caldarium* extract (concentration based on extract dry matter) or TGF-β (10 ng/ml, positive control) relative to the total cell protein content.

Figure 4:
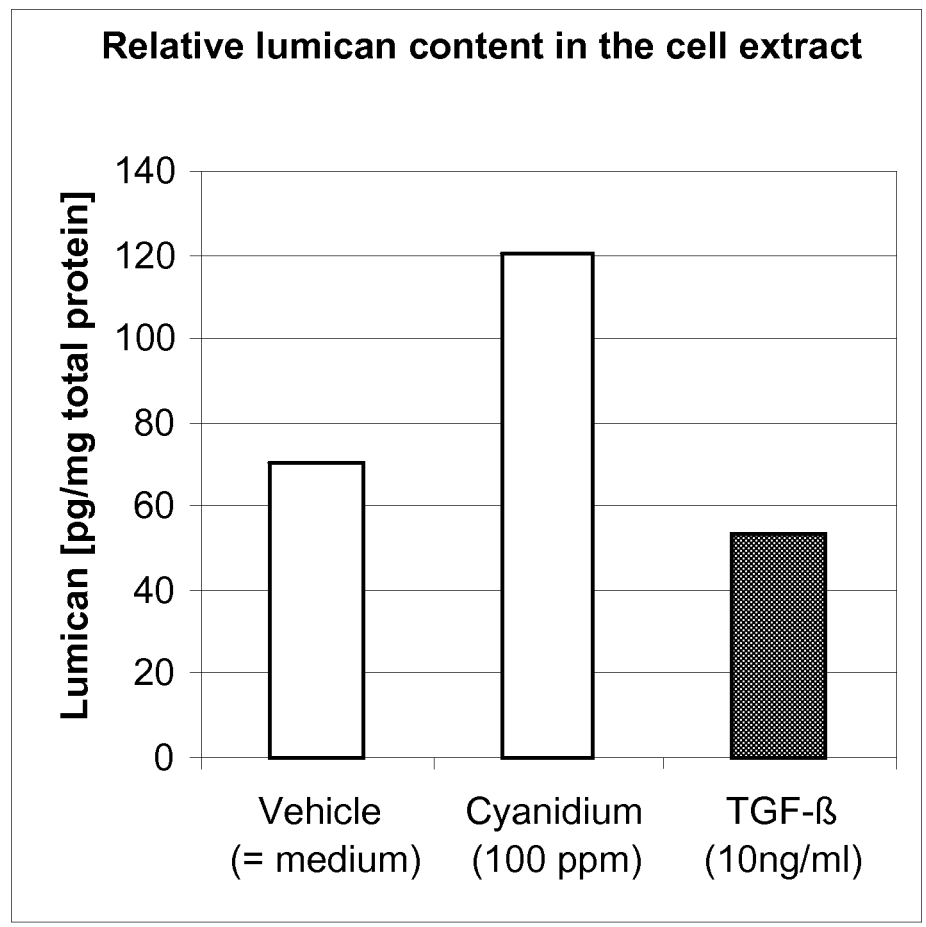

FIG. 4: Lumican protein content in human dermal fibroblasts 24 h after the application of pure medium (vehicle), 100 ppm (=100 µg/ml) *Cyanidium caldarium* extract (concentration based on extract dry matter) or TGF-β (10 ng/ml, positive control) relative to the total cell protein content.

Figure 5:
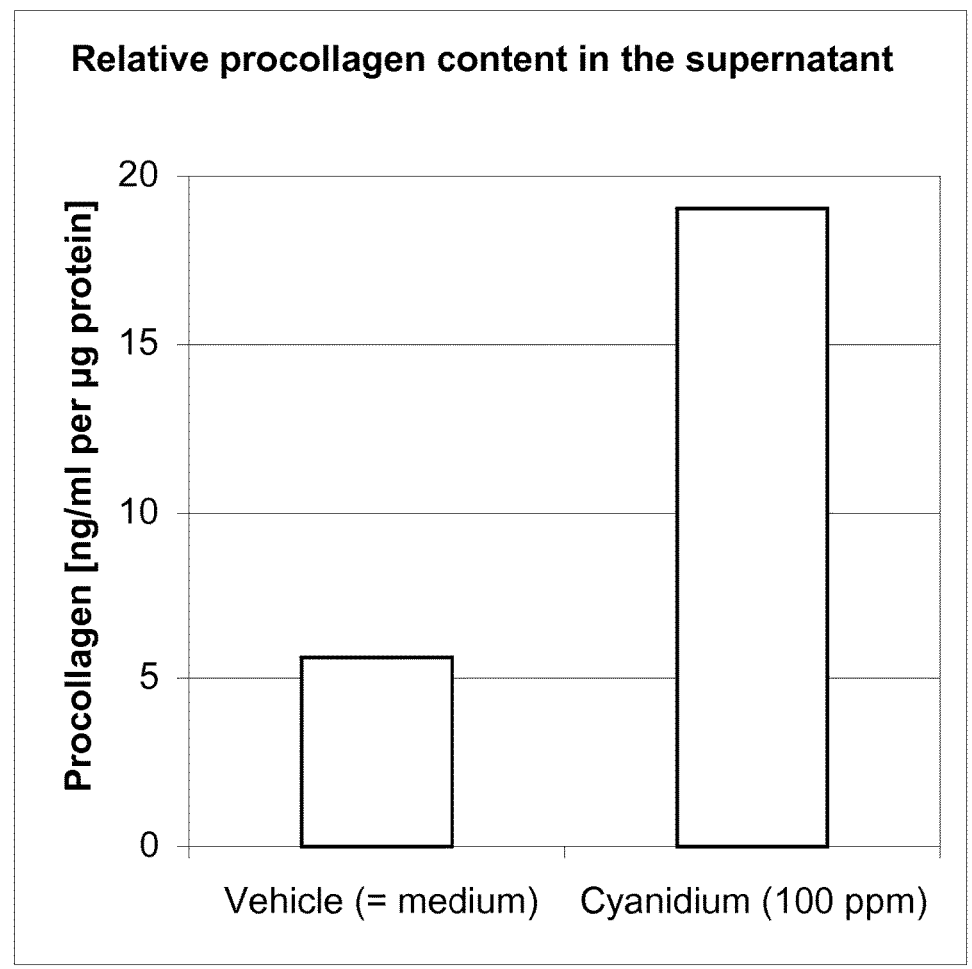

FIG. 5: Procollagen protein content in human dermal fibroblasts 24 h after the application of pure medium (vehicle) or 100 ppm (=100 μg/ml) *Cyanidium caldarium* extract (concentration based on extract dry matter) relative to the total cell protein content.

Figure 6:
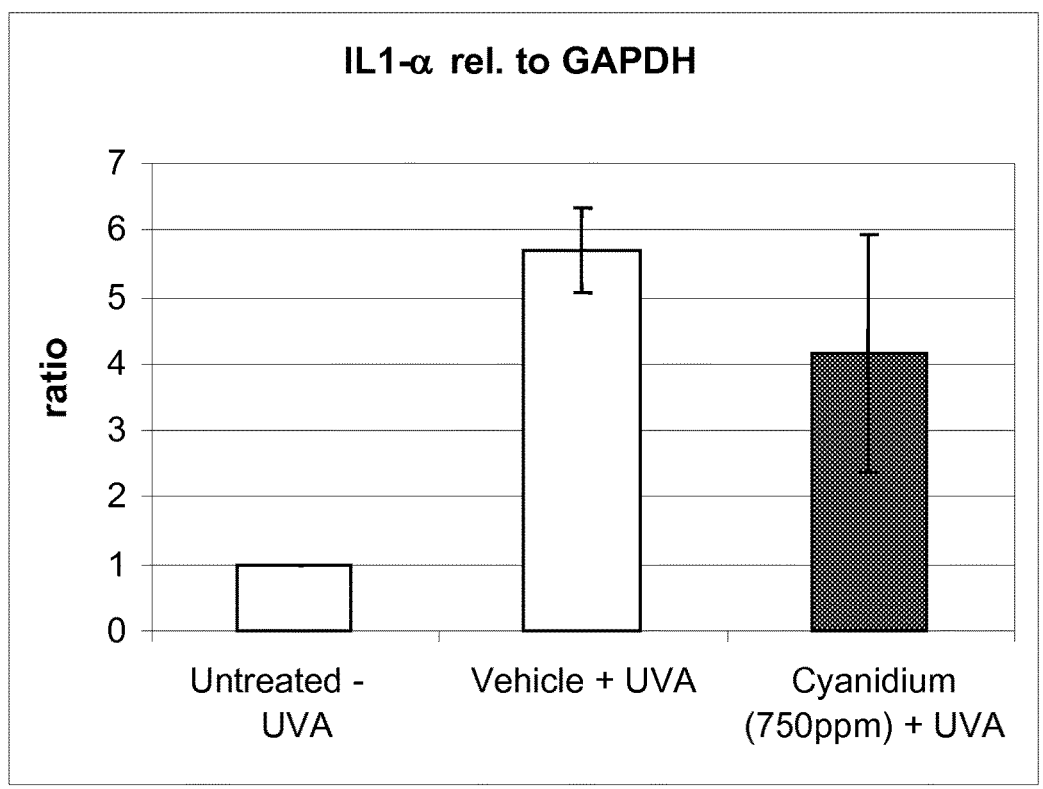

FIG. 6: Gene expression of IL1-α in SkinEthic skin models 24 h after UVA irradiation and application of 750 ppm (=750 μg/ml) *Cyanidium caldarium* extract (concentration based on extract dry matter) or water (vehicle) relative to the GAPDH gene expression.

Figure 7:
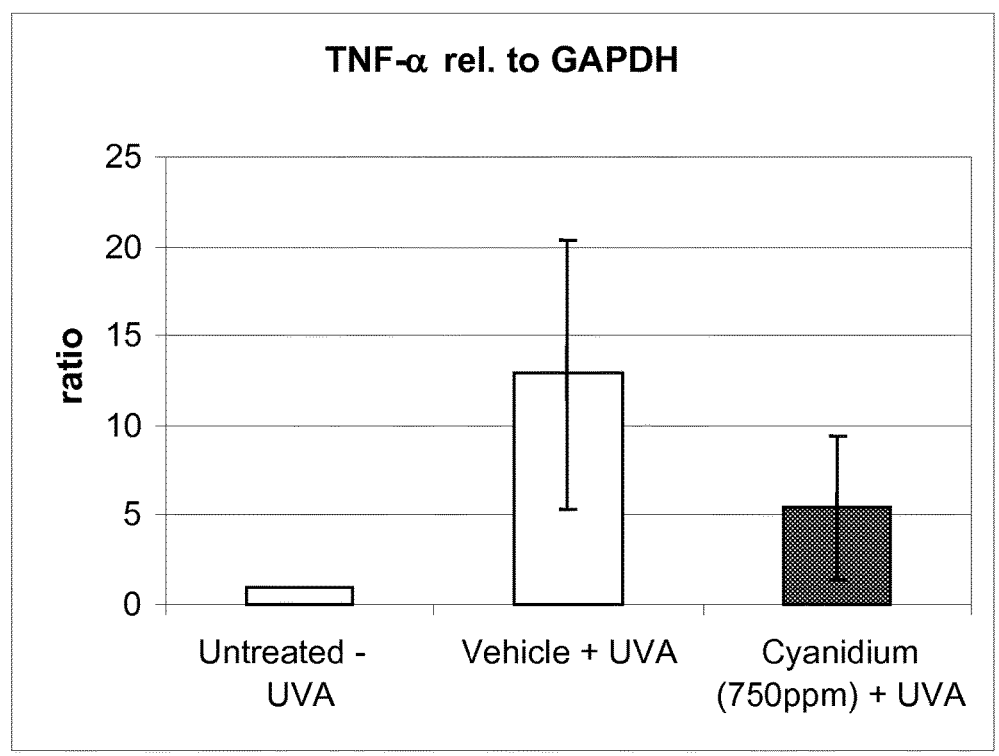

FIG. 7: Gene expression of TNF-α in SkinEthic skin models 24 h after UVA irradiation and application of 750 ppm (=750 μg/ml) *Cyanidium caldarium* extract (concentration based on extract dry matter) or water (vehicle) relative to the GAPDH gene expression.

Figure 8:
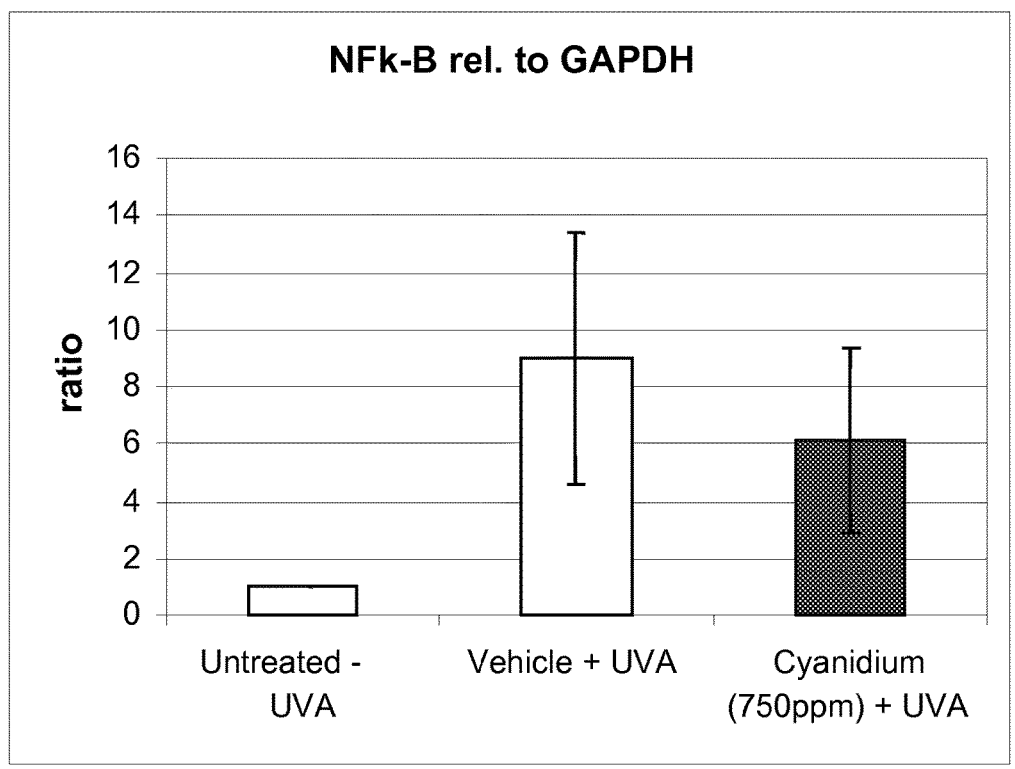

FIG. 8: Gene expression of NFκ-B in SkinEthic skin models 24 h after UVA irradiation and application of 750 ppm (=750 μg/ml) *Cyanidium caldarium* extract (concentration based on extract dry matter) or water (vehicle) relative to the GAPDH gene expression.

Figure 9:
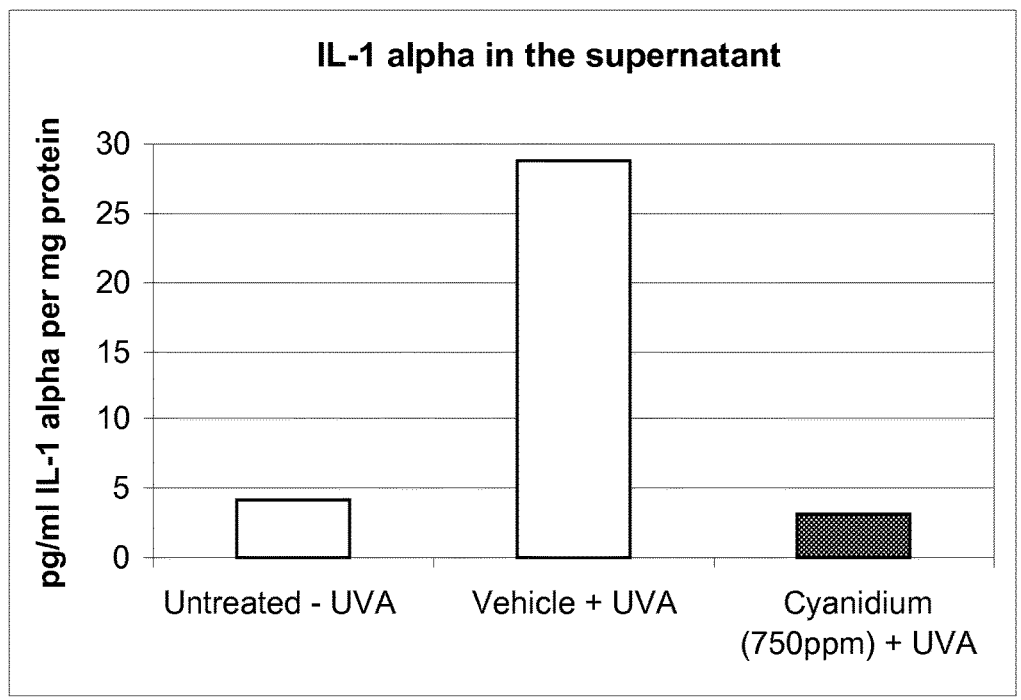

FIG. 9: Interleukin 1-alpha protein content in SkinEthic skin models 24 h after UVA irradiation and application of 750 ppm (=750 μg/ml) *Cyanidium caldarium* extract (concentration based on extract dry matter) or water (vehicle) relative to the total cell protein content.

Figure 10:
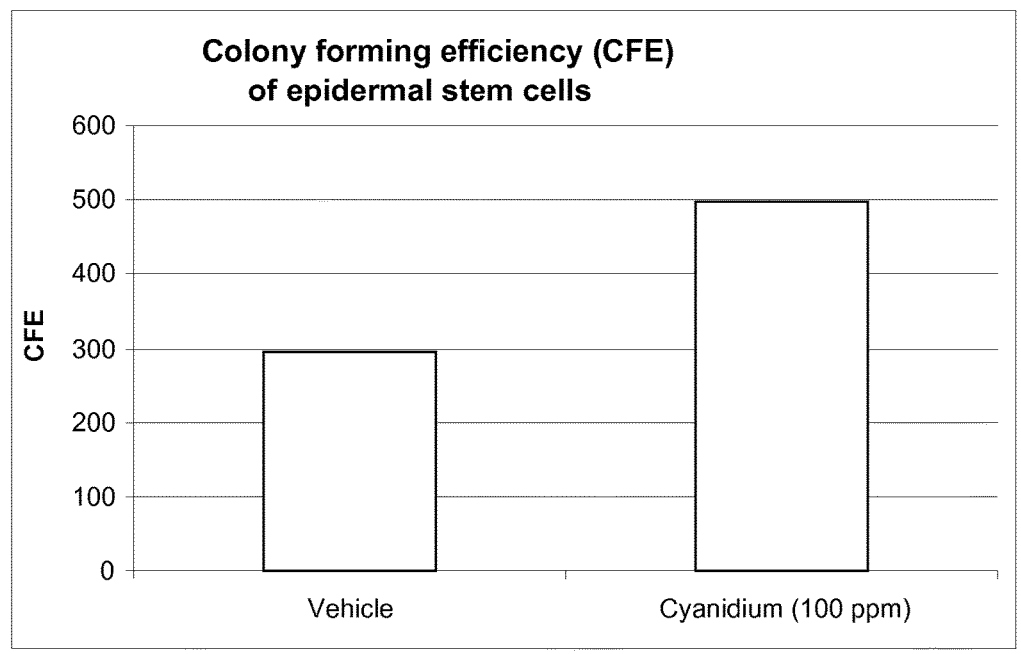

FIG. 10: Effect of *Cyanidium caldarium* extract on the colony formation of epidermal progenitor cells. CFE after the application of 100 ppm (=100 μg/ml) *Cyanidium caldarium* extract (concentration based on extract dry matter) or pure medium (vehicle).

Figure 11:
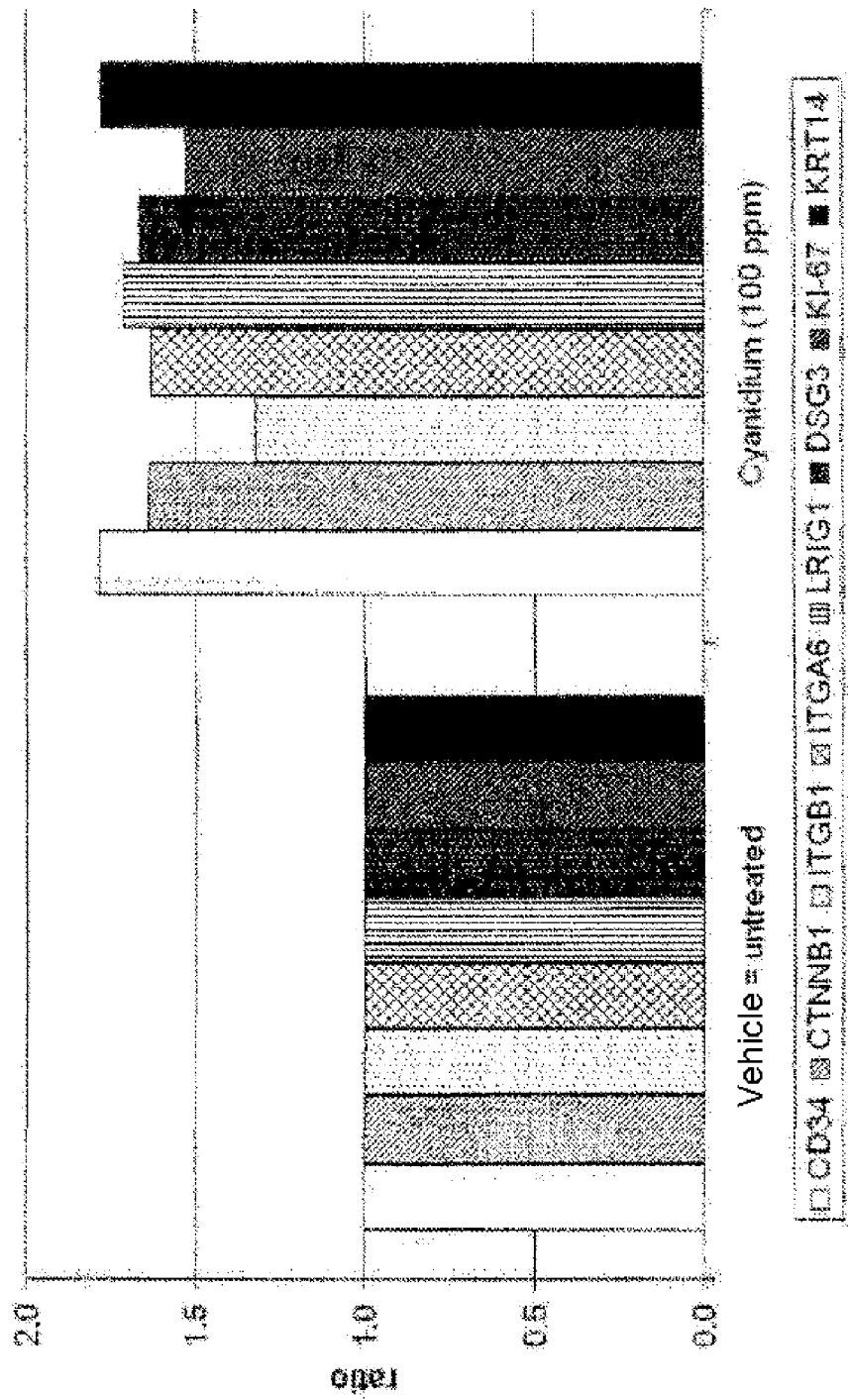

FIG. 11: Gene expression of various genes in epidermal progenitor cells after the application of 100 ppm (=100 μg/ml) *Cyanidium caldarium* extract (concentration based on extract dry matter) or pure medium (vehicle) relative to the B2M gene expression.

Figure 12:
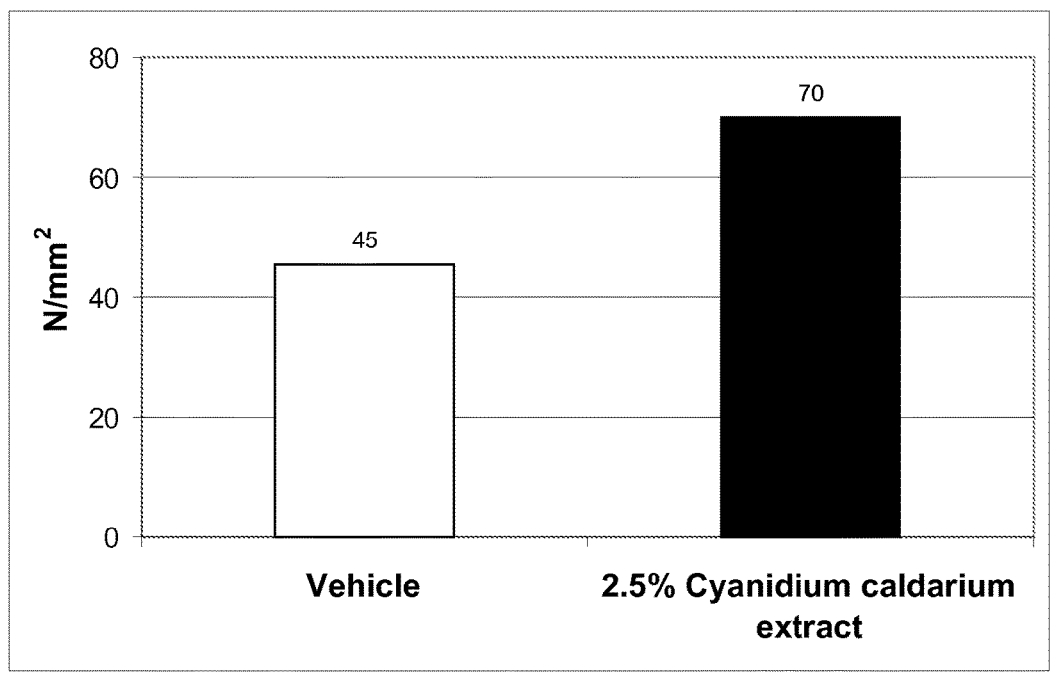

FIG. 12: Means of the parameter E module before and after treatment of the hair samples with leave-on hair conditioner.

Figure 13:
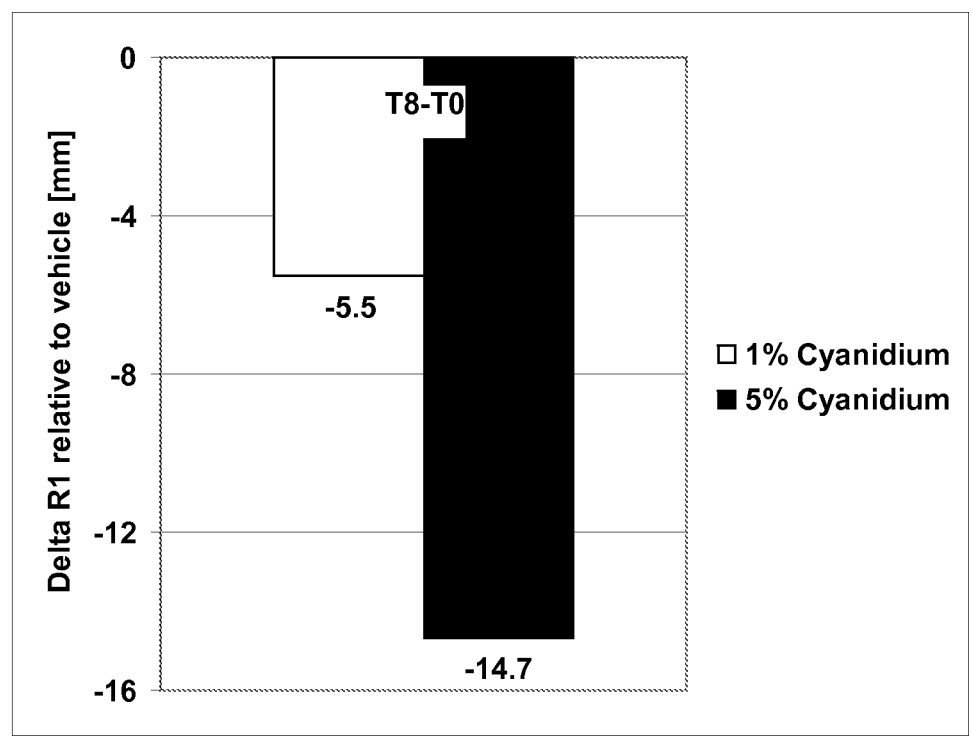

FIG. 13: Skin elasticity parameter R1. Relative change based on the vehicle formulation after eight weeks' treatment with 1% and 5% *Cyanidium caldarium* extract.

Figure 14:
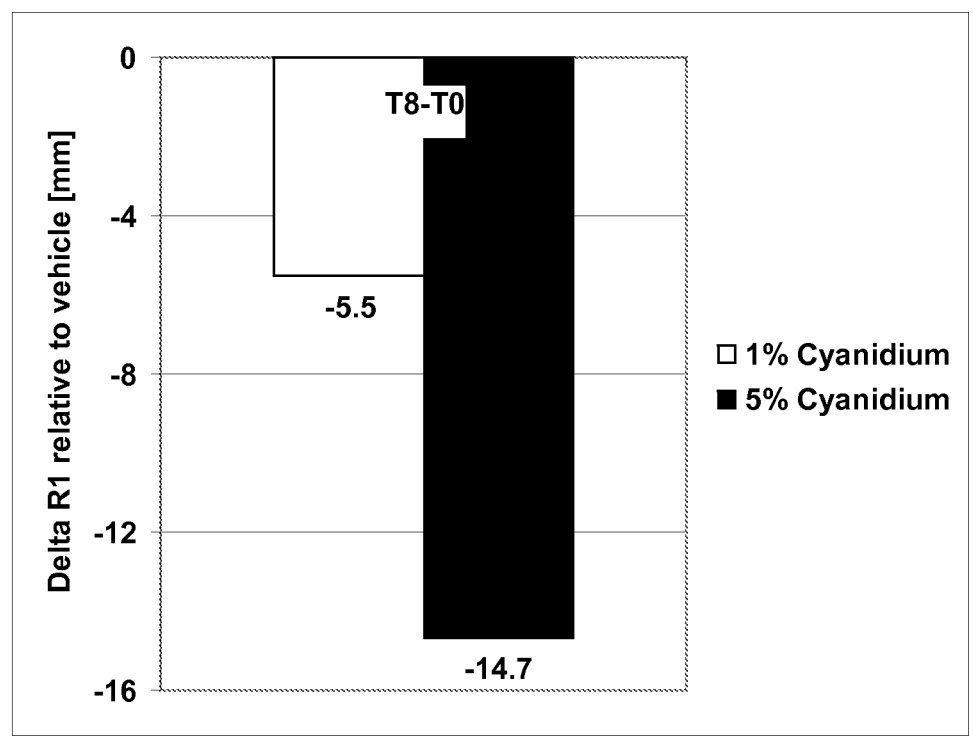

FIG. 14: Skin elasticity parameter R4. Relative change based on the vehicle formulation after eight weeks' treatment with 1% and 5% *Cyanidium caldarium* extract.

Figure 15:
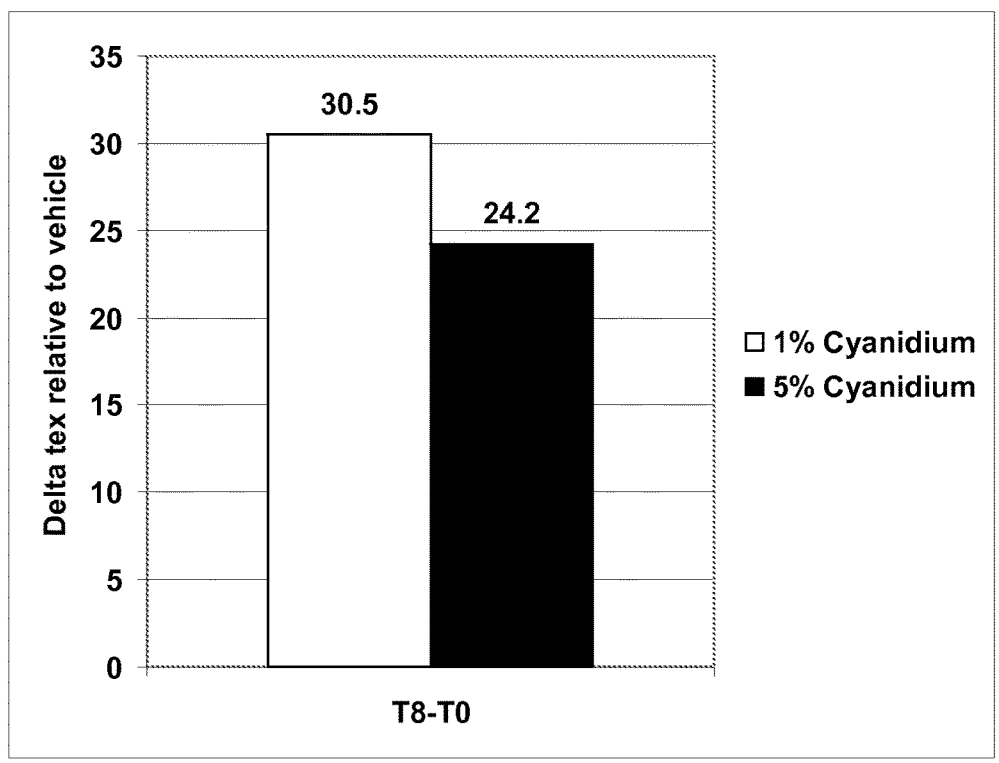

FIG. 15: Skin texture parameter. Relative change based on the vehicle formulation after eight weeks' treatment with 1% and 5% *Cyanidium caldarium* extract.

Figure 16:
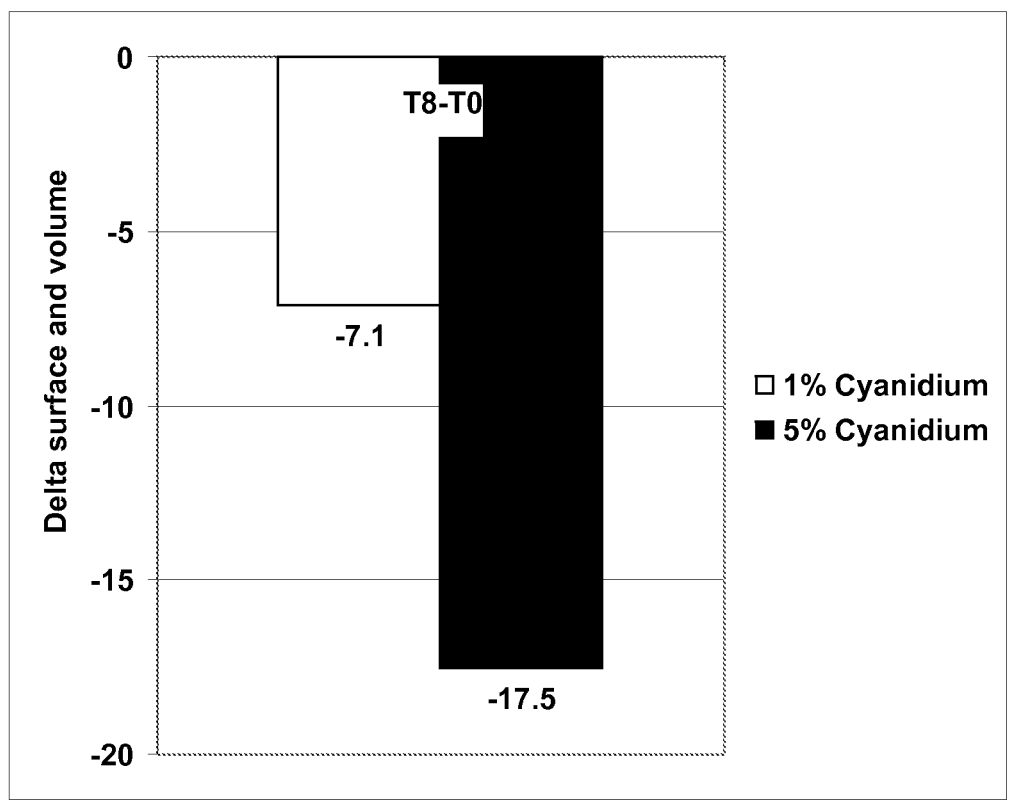

FIG. 16: Skin surface and volume parameter. Relative change based on the vehicle formulation after eight weeks' treatment with 1% and 5% *Cyanidium caldarium* extract.

EXAMPLES

Example 1

Culturing *Cyanidium caldarium*

The preparative *Cyanidium caldarium* biomass production for obtaining the extract takes place in closed photobioreactors as described in detail in DE4411486, DE29607285, WO9105849, WO2010/149154 or DE102009028474A1 (WO2011/018082A2). The culturing method was adapted to the specific growth conditions of the red alga *Cyanidium caldarium* (SAG 16.91). Minimization of the shear stress by selecting suitable pump configurations, continuous light adaptation by a variable design of the light regime during culturing from 50 to 2000 $\mu E*m^{-2}s^{-1}$ and adjusting a pH of <3 allows both high growth rates and reproducible biomass qualities to be achieved.

The culture medium used consisted (per liter of distilled water) of 4.5 g $(NH_4)_2SO_4$, 0.6 g $MgSO_4 \times 7H_2O$, 0.6 g $KH_2PO_4$, 0.03 g $CaCl_2 \times 2H_2O$, 0.01 g $FeSO_4$, 0.018 g ethylenediaminetetraacetic acid disodium dihydrate, 0.005 g $H_3BO_3$, 0.004 $MnCl_2$, 0.00068 g $ZnSO_4 \times 7H_2O$, 0.00052 g $Na_2MoO_4 \times 2H_2O$, 0.00008 g $CuSO_4 \times 5H_2O$, 0.00008 g $NaVO_3 \times 4H_2O$, 0.00064 g $CoCl_2 \times 6H_2O$. The pH of the medium was brought to 2-3 by adding 1 N $H_2SO_4$ and/or by regulating the $CO_2$ concentration. For a preculture, a 5 l Erlenmeyer flask was filled with 1 l of medium and inoculated with *Cyanidium caldarium* (SAG 16.91) stock culture. The culture was incubated at 30° C. underneath fluorescent tubes with 140 $\mu E*m^{-2}s^{-1}$, with gentle shaking. The growth of the algae culture was monitored by absorption at 550 nm. As soon as the growth had reached the exponential phase (OD 1.0), the cells were harvested by centrifugation for 10 minutes at 5000 rpm, and the pellets were washed with distilled water. The wet biomass was stored at −20° C. until further use.

Example 2

Aqueous Extraction of *Cyanidium caldarium*

Harvesting from photobioreactors is done as described for example in DE10136645 (EP 1277831) or WO9105849.

The use of ultrasound for disrupting microalgae cells has been described and can be reproduced, inter alia, with reference to US2009069213, example 3 and US2008299147, example 3. Insoluble components were separated off by filtration with 200 μm bag filter. 1.0% of Rokonsal BS is added to the aqueous extract for preservation purposes. The dry matter (105° C.) of the aqueous *Cyanidium caldarium* extract as determined by Sartorius MA30 Moisture Analyzer gave a value of 2.5%.

Example 3

Detection of GABA in *Cyanidium caldarium*

GABA was detected by high-performance liquid chromatography (HPLC) following derivatization by ortho-phthalic dialdehyde (OPA). The HPLC apparatus was composed of Jasco PU 2080Plus pump, JascoAS 2055Plus autosampler, Jasco FP-2020Plus fluorescence detector and Jasco ChromPass 1.8.6.1 integrator (Jasco Germany GmbH, Gross-Umstadt, Germany). The stationary phase used was aZorbax Eclipse XDB-C18, 4.6×150 mm, 3.5 μm column (Agilent Technologies, Inc.) at a temperature of 40° C. The following gradient was used as the mobile phase (A: 2% acetonitrile, 2% tetrahydrofuran, 96%50 mM phosphoric acid, brought to pH 7.5 with NaOH); B: 65% acetonitrile, 35% water): 0-2 min 20% B constant, 2-8 min 20-40% B linear, 8-11 min 40-100% B linear, 11-38 min 100% B constant. The flow rate was 1.5 ml/min. 5 μL of the analyte together with 15 μL of OPA reagent (1 mL phthalic dialdehyde reagent, Solution Complete, Sigma-Aldrich P0532 and 0.5 μL mercaptoethanol) were injected. The absorption wavelength was 340 nm and the emission wavelength 455 nm. The internal standard used was 1,6-diaminohexane. The analyte was prepared by diluting 1 ml of the aqueous *Cyanidium caldarium* extract to 100 ml with water.

A typical value for GABA in the *Cyanidium caldarium* extract was 0.090%. This value corresponded to 3.3% of GABA based on *Cyanidium caldarium* dry matter.

Example 4

Gene Expression Analysis of *Cyanidium caldarium* Extract on Human Dermal Fibroblasts by Means of Gene Chip Study Method:

In the present example, the effect of *Cyanidium caldarium* extract on the gene expression in fibroblasts (normal human dermal fibroblasts, NHDFs) was studied. To this end, primary human dermal fibroblasts (human dermal fibroblasts derived from neonatal skin (HDF), cryocenserved, Lifeline Cell Technology, obtained from CellSystems® Biotechnologie Vertrieb GmbH, St. Katharinen, Germany) were first grown in Minimum Essential Medium (MEM) supplemented with Earle's salts (EMEM) (PAA Laboratories GmbH, Pasching, Austria) with the addition of 10% foetal calf serum (FBS—fetal bovine serum, (Invitrogen Ltd, UK), 1% nonessential amino acids (NEAA (100×)—non essential amino acids, PAA, Pasching, Austria), 1% L-glutamine (100×) (Invitrogen Ltd, UK) and 1% penicillin/streptomycin (5000 U/ml penicillin and 5000 µg/ml streptomycin, Invitrogen Ltd, UK) at 37° C. and 5% $CO_2$. For gene expression studies, the cells were sown in 6-well plates and grown to subconfluence (maximum 60%).

Thereafter, the medium was drawn off from the cells and replaced by fresh medium with *Cyanidium caldarium* extract. The final concentration of *Cyanidium caldarium* extract in the medium was 100 ppm (=100 µg/ml, based on *Cyanidium caldarium* extract dry matter). As a control, the cultures were grown without active substance, only with medium (vehicle). All cultures were performed in triplicate (3 biological replications).

After the cells had been cultured for 24 hours, the medium was drawn off and the cells were lysed by the addition of RNeasy Lysis Buffer (Qiagen, Hilden, Germany). The total RNA was isolated following the manufacturer's instructions. In summary, the total RNA was isolated by means of RNeasy Mini Kit (Qiagen, Hilden, Germany). The RNA quality was determined by the Agilent 2100 Bioanalyzer and Agilent RNA 6000 Nano Kit (Agilent Technologies, Inc., Santa Clara, Calif., USA). The three biological replications were pooled, and the concentration of the pooled samples was determined by photometric measurement at 260/280 nm.

Gene expression was analysed by means of Affymetrix GeneChip expression analyses including standard data evaluation following the manufacturer's instructions (Human Gene 1.0 ST Array, Expression Console Software, AFFYMETRIX, INC., Santa Clara, Calif., USA).

The results are shown in Table 1

TABLE 1

Synopsis of genes with at least 2-fold upregulation or downregulation in human dermal fibroblasts 24 h after the application of 100 ppm (=100 µg/ml) *Cyanidium caldarium* extract (concentration based on extract dry matter).

| Gene | Protein/function | Regulation by 100 ppm of *Cyanidium* extract |
|---|---|---|
| ELN | Elastin; besides fibrillin main component of elastic fibres | +2.4 |
| FBN2 | Fibrillin; besides elastin main component of elastic fibres | +2.2 |
| COL3A1 | Collagen type III alpha-1chain; collagen type III is a fibrillary collagen which is present in the skin in close association with the main collagen type I collagen. | +1.8 |
| COL11A1 | Collagen type XI alpha-1 chain | +2.5 |
| LUM | Lumican; belongs to the family of the small leucine-rich proteoglycans (SLRP; small leucine rich proteoglycan); interacts with collagen fibrils thereby regulating the interfibrillary distances | +2.0 |
| ACAN | Aggrecan; large aggregating proteoglycan; important structural component of the extracellular matrix | +2.7 |
| SDC2 | Syndecan; a heparan sulphateproteoglycan; important for cell proliferation, cell migration and cell matrix interactions | +2.1 |
| CTGF | Connective tissue growth factor; central factor for controlling the formation of the extracellular matrix | +2.4 |
| SULF1 | Sulphatase; removal of sulphate residues from heparan sulphate; signal transduction | +2.7 |
| MMP1 | Matrix metalloprotease 1; degradation of collagen types I, II, III | −5.7 |
| MMP3 | Matrix metalloprotease 3; degradation of fibronectin, laminin, collagentypes III, IV, IX, X | −2.1 |

The gene chip studies in human dermal fibroblasts demonstrated a uniform stimulation of elastin (ELN) and fibrillin (FBN2), the most important structural components of elastic fibres, by the addition of *Cyanidium caldarium* extract. Furthermore, the gene expression of important structural proteins of the connective tissue, collagen III and XI (COL3A1, COL11A1), was increased. Other proteins such as aggrecan (ACAN), syndecan (SDC2) and lumican (LUM) have a structure-imparting function or help with organizing interactions between various extracellular matrix (ECM) components and fibroblast cells. The genes of these proteins (LUM, ACAN, SDC2), too, were upregulated by a *Cyanidium caldarium* extract. The degradation of extracellular matrix components was prevented efficiently by the downregulation of matrix metalloprotease 1 (MMP-1) and matrix metalloprotease 3 (MMP-3). Moreover, *Cyanidium caldarium* extract is a potential mediator of the connective tissue growth factor (CTGF). To summarize, the described gene regulation demonstrates that the cosmetic according to the invention strengthens the overall structure of the ECM rather than merely the structure of the individual ECM components.

Example 5

Gene and Protein Expression Analysis of *Cyanidium caldarium* Extract on Human Dermal Fibroblasts by Means of qRT-PCR and ELISA Method:

In the present example, the effect of *Cyanidium caldarium* extract on the gene and protein expression in fibroblasts (normal human dermal fibroblasts, NHDFs) was studied.

To this end, primary human dermal fibroblasts (human dermal fibroblasts derived from neonatal skin (HDF), cryocenserved, Lifeline Cell Technology, obtained from Cell-Systems® Biotechnologie Vertrieb GmbH, St. Katharinen, Germany) were first grown in Minimum Essential Medium (MEM) supplemented with Earle's salts (EMEM) (PAA Laboratories GmbH, Pasching, Austria) with the addition of 10% foetal calf serum (FBS—fetal bovine serum, Invitrogen Ltd, UK), 1% nonessential amino acids (NEAA (100×)—non essential amino acids, PAA, Pasching, Austria), 1% L-glutamine (100×) (Invitrogen Ltd, UK) and 1% penicillin/streptomycin (5000 U/ml penicillin and 5000 µg/ml streptomycin/ml, Invitrogen Ltd, UK) at 37° C. and 5% $CO_2$ until a suitable cell count had been achieved. For gene expression studies, the cells were sown in 6-well plates and grown to subconfluence (maximum 60%).

Thereafter, the medium was drawn off from the cells and replaced by fresh medium with *Cyanidium caldarium* extract. The final concentration of *Cyanidium caldarium* extract in the medium was 100 ppm (=100 µg/ml, based on extract dry matter). As a control, the cultures were grown without active substance, only with medium (vehicle) or with 10 ng/ml transforming growth factor beta 3 (TGFβ-3) as the positive control. All cultures were performed in triplicate (3 biological replications). To study the gene expression, the medium was drawn off after 24 hours' culturing, and the cells were lysed by addition of RNeasy Lysis Buffer (Qiagen, Hilden, Germany). The total RNA was isolated following the manufacturer's instructions. To summarize, the total RNA was isolated by means of the RNeasy Mini Kit (Qiagen, Hilden, Germany). The RNA quality and quantity was determined by means of an Agilent 2100 Bioanalyzer and Agilent RNA 6000 Nano Kit (Agilent Technologies, Inc., Santa Clara, Calif., USA).

Each sample was analysed for the gene expression of collagen (COL1A1), elastin (ELN), matrix metalloproteinase-1 (MMP-1), fibrillin-2 (FBN2), connective tissue growth factor (CTGF), syndecan-2 (SDC2) and lumican (LUM) by means of quantitative real-time polymerase chain reaction (qRT-PCR). To this end, in each case 100 ng of total RNA were employed for the cDNA synthesis with the Super Script III First Strand Synthesis Super Mix (Invitrogen Ltd, UK) being employed in accordance with the manufacturer's instructions. The Quanti Tect SYBR Green PCR Kit (Qiagen, Hilden, Germany) was employed in accordance with the manufacturer's instructions for the PCR reaction. Besides the expression of the target genes, the expression of the glyceraldehyde-3-phosphate dehydrogenase (GAPDH) gene, too, was determined quantitatively by way of reference. The following primer pairs were employed in each case for the target genes:

COL1A1: 60° C.
    Seq. ID No. 01
5'-GCCTCGGAGGAAACTTTG-3'

Seq. ID No. 02
5'-GACCCATGGGACCTGAAG-3'

ELN: 56° C.
    Seq. ID No. 03
5'-GCCCAGTTTGGCCTAGTG-3'

Seq. ID No. 04
5'-CAGCAGCACCGTATTTAG-3'

MMP-1: 60° C.
    Seq. ID No. 05
5'-TGGGAGCAAACACATCTGA-3'

Seq. ID No. 06
5'-ATCACTTCTCCCCGAATCGT-3'

FBN2: 60° C.
    Seq. ID No. 07
5'-TCGCCCGGCAGCAAACTCAG-3'

Seq. ID No. 08
5'-TCACACCGCTCACAGGGGCT-3'

CTGF: 60° C.
    Seq. ID No. 09
5'-CAGGCTAGAGAAGCAGAGCC-3'

Seq. ID No. 10
5'-TGGAGATTTTGGGAGTACGG-3'

SDC2: 60° C.
    Seq. ID No. 11
5'-CGTGGATCCTGCTCACCT-3'

Seq. ID No. 12
5'-CAATGGAGCTGTTGTCAAGG-3'

LUM: 56° C.
    Seq. ID No. 13
5'-GGTTGAGCTGGATCTGTCCT-3'

Seq. ID No. 14
5'-AGTAGGATAATGGCCCCAGG-3'

GAPDH: 60° C.
    Seq. ID No. 15
5'-ACCACAGTCCATGCCATCAC-3'

Seq. ID No. 16
5'-TCCACCACCCTGTTGCTGTA-3'

The PCR reactions were performed using an Opticon 1 (MJ Research, Waltham, Mass., USA). In all PCRs, duplicate determinations of the biological triplicates were carried out, and means of all measurements were calculated for the evaluation. The PCR protocol had the following profile: step 1), 15 minutes activation of the hot-start polymerase at 95° C.; step 2), 15 seconds denaturation at 94° C.; step 3), 30 seconds primer annealing at 56° C. or 60° C., depending on the primer pair; step 4), 30 seconds extension at 72° C. The number of cycles for steps 2)-4) was 44. The 2(-delta delta C(T)) method (Livak K J, and Schmittgen T D: Analysis of relative gene expression data using real time quantitative PCR and the 2 (-delta delta C(T)) method. Methods 2001, 25: 402-408) was employed for the relative comparison of the gene expression.

To study the protein expression, the medium was drawn off after 24 hours of culturing, and the cells were lysed by ultrasonic treatment (10 seconds at 34-40 kHz). The total protein content of the sonicates was determined by the Bradford test (Bio-Rad Protein Assay, Bio-Rad Laboratories, Inc., Hercules, Calif., USA) following the manufacturer's instructions. Using ELISA technology, each sample was analysed for the protein content of elastin in the cell extract (human Elastin ELISA Kit, ABO Swiss Co., Ltd, Fujian, CN) and lumican (human Lumican ELISA Kit, ABO Swiss Co., Ltd, Fujian, CN) or procollagen (Procollagen Type I C-Peptide (PIP) EIA Kit, TAKARA BIO INC., JP) in the culture supernatant, following the instructions of the manufacturer in question. The absolute protein quantity was determined in relation to the total protein. The results are shown in FIGS. 1 to 5 and demonstrate that the treatment of the keratinocytes with *Cyanidium caldarium* extract significantly stimulates the gene expression of COL1A1, ELN, FBN2, SDC2 and LUM. The expression of the MMP-1 gene was downregulated significantly. Moreover, treatment of the cells for 24 hours with *Cyanidium caldarium* extract had a positive effect at the protein level not only on elastin, but also on lumican and procollagen.

To summarize, the gene regulation described corroborates the results of the gene chip analysis. The cosmetic according to the invention strengthens the overall structure of the ECM rather than merely its individual components.

Example 6

Effect of *Cyanidium caldarium* Extract on UVA-Stressed Human Epidermis Models

Method:

In the present example, the effect of *Cyanidium caldarium* extract on the gene and protein expression in epidermis skin models (reconstituted human epidermis) was studied.

To this end, skin models (reconstructed epidermis of normal human keratinocytes, RHE/S/17, SkinEthic laboratories, Nice, F) were cultured for 24 hours at 37° C. and 5% $CO_2$ in maintenance medium (SkinEthic laboratories, Nice, F). For gene and protein expression studies, the skin models were subsequently treated topically within each case 50 µl of *Cyanidium caldarium* extract or the respective controls. After 1 hour, the sample excess was removed by blotting. The final concentration of *Cyanidium caldarium* extract in the medium was 750 ppm (=750 µg/ml, based on extract dry matter). Culturing was performed without active substance or only with water (vehicle) by way of control. All cultures were performed in triplicate (3 biological replications). After 24 hours of culturing, the skin models were irradiated with a dose of 40 $J/cm^2$ at 9.5 $mW/cm^2$ UVA. Thereafter, the medium was exchanged, and the test substances or controls were reapplied. 24 hours after the second application, the skin models were transferred into RNAlater (RNA Stabilization Reagent, Qiagen, Hilden, Germany). The supernatant of the skin models (medium) was frozen (−80° C.) with addition of Complete Protease Inhibitor Cocktail Tablets (F. Hoffmann-La Roche Ltd, Basle, CH) for further analysing the protein expression.

Total RNA from the skin models was isolated by means of the RNeasy Lipid Tissue Mini Kit (Qiagen, Hilden, Germany) following the manufacturer's instructions. The RNA quality and quantity was determined using an Agilent 2100 Bioanalyzer and Agilent RNA 6000 Nano Kit (Agilent Technologies, Inc., Santa Clara, Calif., USA).

The gene expression of interleukin 1-alpha (IL1-α), tumour necrosis factor-alpha (TNF-α) and nuclear factor kappa-light-chain-enhancer of activated B cells (NFκ-B) of each sample was studied by means of quantitative real-time polymerase chain reaction (qRT-PCR). To this end, 100 ng of total RNA were employed in each case for the cDNA synthesis, with the Super Script III First Strand Synthesis Super Mix (Invitrogen Ltd, UK) being employed, following the manufacturer's instructions. The Quanti Tect SYBR Green PCR Kit (Qiagen, Hilden, Germany) was employed for the PCR reaction, following the manufacturer's instructions. The expression of glyceraldehyde-3-phosphate dehydrogenase (GAPDH), too, was determined quantitatively by way of reference gene. The following primer pairs were employed in each case:

```
NFκ-B:
                                   Seq. ID No. 17
      5'-CCTGGATGACTCTTGGGAAA-3'

Seq. ID No. 18
      5'-TCAGCCAGCTGTTTCATGTC-3'

TNF-α:
                                   Seq. ID No. 19
      5'-CTCTGGCCCAGGCAGTCAGA-3'

Seq. ID No. 20
      5'-GGCGTTTGGGAAGGTTGGAT-3'

IL1-α:
                                   Seq. ID No. 21
      5'-CACTCCATGAAGGCTGCATGG-3'

Seq. ID No. 22
      5'-ACCCAGTAGTCTTGCTTTGTGG-3'

GAPDH:
                                   Seq. ID No. 23
      5'-ACCACAGTCCATGCCATCAC-3'

Seq. ID No. 24
      5'-TCCACCACCCTGTTGCTGTA-3'
```

The PCR reactions were performed using an Opticon 1 (MJ Research, Waltham, Mass., USA). In all PCRs, duplicate determinations of the biological triplicates were carried out, and means of all measurements were calculated for the evaluation. The PCR protocol had the following profile: step 1), 15 minutes activation of the hot-start polymerase at 95° C.; step 2), 15 seconds denaturation at 94° C.; step 3), 30 seconds primer annealing at 60° C.; step 4), 30 seconds extension at 72° C. The number of cycles for steps 2)-4) was 44. The 2(-delta delta C(T)) method (Livak K J, and Schmittgen T D: Analysis of relative gene expression data using real time quantitative PCR and the 2 (-delta delta C(T)) method. Methods 2001, 25: 402-408) was employed for the relative comparison of the gene expression.

To study the protein expression, the supernatant of the skin models was drawn off and the total protein from the skin models was isolated in the form of a combined protocol in addition to the RNA by means of RNeasy Lipid Tissue Mini Kit (Qiagen, Hilden, Germany). Specifically, the residual water phase was removed from the RNA isolation samples. 0.3 ml of 100% ethanol was added, and the samples were inverted and incubated at room temperature (IT) for 2-3 min. Thereafter, the samples were centrifuged at 2000×g for 2 min at 4° C. The supernatant with the proteins was placed into a fresh tube (2 ml). The proteins were precipitated by addition of 1.5 ml of isopropanol and incubated at IT for 10 min. Thereafter, the samples were centrifuged at 12 000×g for 10 min at 4° C. The pellet was taken up in 2 ml of guanidine/ethanol solution and incubated at IT for 20 min. Thereafter, the samples were centrifuged at 7500×g for 5 min at IT. This wash step was repeated twice. After the addition of 2 ml of ethanol (100%) the samples were incubated at IT for 20 min. Thereafter, the samples were centrifuged at 7500×g for 5 min at IT. The pellet was dried in the air for 5-10 min, taken up in 500 μl of urea/DTT solution and incubated at IT for 1 h. To dissolve the proteins, the samples were heated at 95° C. for 3 minutes.

The total protein content was determined by Bradford test (Bio-Rad Protein Assay, Bio-Rad Laboratories, Inc., Hercules, Calif., USA) following the manufacturer's instructions. By means of ELISA technique, each sample was analysed for the protein content of interleukin 1-alpha (IL1-α) (HumanIL-1α ELISA Kit, (Invitrogen Ltd, UK) in the culture supernatant following the instructions of the respective manufacturer. The absolute protein quantity was determined in relation to the total protein.

The results of this study are shown in FIGS. 6 to 9 and demonstrate that *Cyanidium caldarium* extract is capable of reducing the UVA-induced expression of proinflammatory markers at the molecular level. Thus, *Cyanidium caldarium* extract re-established the epidermal homeostasis, which is regulated in the main by NFκB and also TNF-α and IL-1α, in UVA-stressed skin models.

Example 7

Effect of *Cyanidium caldarium* Extract on Epidermal Stem Cells

Method:

In the present example, the activity of *Cyanidium caldarium* extract on epidermal stem cells (epidermal keratinocyte progenitors, HPEK) was studied.

To this end, CnT-57 NHEK progenitor cells (normal human epidermal keratinocyte progenitor cells (HPEKp05)), derived from neonatal foreskin and cryoconserved at P2, CELLnTEC Advanced Cell Systems AG, Berne, Switzerland) were first cultured in supplemented CnT-57 medium (Progenitor Cell Targeted Epidermal Keratinocyte Medium based on low Bovine Pituitary Extract (BPE), CELLnTEC Advanced Cell Systems AG, Berne, Switzerland)+2% penicillin/streptomycin solution (5000 U/ml penicillin and 5000 μg/ml streptomycin/ml, Invitrogen Ltd, UK) at 37° C. and 5% $CO_2$ until a suitable cell density had been reached.

To determine the colony forming efficiency (CFE), the cells were subsequently grown at low seeding density (800 cells/25 cm$^2$) for 8 days in the presence of *Cyanidium caldarium* extract.

The final concentration of *Cyanidium caldarium* extract in the medium was 100 ppm (=100 μg/ml, based on algae dry matter). As a control, culturing was done without active substance, only with medium (vehicle). All the cultures were performed in triplicate (3 biological replications).

After the cell culture medium had been drawn off, the cell colonies were stained with haematoxylin/eosin (CnT-ST-100 Stain Kit, CELLnTEC Advanced Cell Systems AG, Berne, Switzerland) following the manufacturer's instructions. The colony-forming units were counted under the microscope.

For gene expression studies, the cells were furthermore grown at a seeding density of 3000 cells/25 cm$^2$ for 7 days in the presence of *Cyanidium caldarium* extract until subconfluence (75%) had been reached.

The final concentration of *Cyanidium caldarium* extract in the medium was 100 ppm (=100 μg/ml, based on extract dry matter). As a control, the cultures were grown without active substance, only with medium (vehicle). All cultures were performed in triplicate (3 biological replications).

To study the gene expression, the medium was drawn off and the cells were lysed by the addition of RNeasy Lysis Buffer (Qiagen, Hilden, Germany). Total RNA was isolated following the manufacturer's instructions. To summarize, the total RNA was isolated by means of the RNeasy Mini Kit (Qiagen, Hilden, Germany). The RNA quality and quantity were determined by the Agilent 2100 Bioanalyzer and Agilent RNA 6000 Nano Kit (Agilent Technologies, Inc., Santa Clara, Calif., USA).

Each sample was analysed for the gene expression of CD34 (haematopoietic progenitor cell antigen), CTNNB1 (β-catenine), ITGB1 (integrin beta-1), ITGA6 (integrin alpha-6), LRIG1 (leucine-rich repeats and immunoglobulin-like domains protein 1), DSG3 (desmoglein-3), MKI67 (antigen KI-67) and KRT14 (keratin-14) by means of quantitative real-time polymerase chain reaction (qRT-PCR). To this end, 100 ng of total RNA were employed in each case for the cDNA synthesis, with the Superscript VILO cDNA Synthesis Kit (Invitrogen Ltd, UK) being employed following the manufacturer's instructions. The QuantiFast SYBR Green PCR Kit (Qiagen, Hilden, Germany) was employed for the PCR reaction, following the manufacturer's instructions. Besides the expression of the target genes, the expression of the B2M (β2-microglobulin) gene, too, was determined quantitatively by way of reference. The following primer pairs were employed in each case for the genes:

```
CD34:
                               Seq. ID No. 25
5'-CCACCAGAGCTATTCCCAAAAG-3'

Seq. ID No. 26
5'-GCGGCGATTCATCAGGAAAT-3'

CTNNB1:
                               Seq. ID No. 27
5'-TGCCAAGTGGGTGGTATAGA-3'

Seq. ID No. 28
5'-TCAGATGACGAAGAGCACAGA-3'

ITGB1:
                               Seq. ID No. 29
5'-ATGTGAATGCCAAAGCGAAG-3'

Seq. ID No. 30
5'-CTACCAACACGCCCTTCATT-3'

ITGA6:
                               Seq. ID No. 31
5'-CTCTTCGGCTTCTCGCTG-3'

Seq. ID No. 32
5'-CCCGTTCTGTTGGCTCTCT-3'

LRIG1:
                               Seq. ID No. 33
5'-GACCTGCCCTCCTGGAC-3'

Seq. ID No. 34
5'-GTAGGTTCGGCAAGTCCTCA-3'

DSG3:
                               Seq. ID No. 35
5'-CGGCCTGCTGCTCCTTGGTC-3'

Seq. ID No. 36
5'-CACCGCTGTGCCTCTGGCAT-3'

KI-67:
                               Seq. ID No. 37
5'-ATCGTCCCAGGTGGAAGAGTT-3'

Seq. ID No. 38
5'-ATAGTAACCAGGCGTCTCGTGG-3'
```

-continued

```
KRT14:
                                         Seq. ID No. 39
5'-GGCCTGCTGAGATCAAAGAC-3'

Seq. ID No. 40
5'-TCTGCAGAAGGACATTGGC-3'

B2M:
                                         Seq. ID No. 41
5'-GTGCTCGCGCTACTCTCTCT-3'

Seq. ID No. 42
5'-TTCAATGTCGGATGGATGAA-3'
```

The PCR reactions were performed using a StepOne-Plus™ Real-Time PCR system (Life Technologies Corporation, CA, USA). For all PCRs, duplicate determinations of the biological triplicates were carried out, and means of all measurements were calculated for the evaluation. The PCR protocol had the following profile: step 1), 5 minutes activation of the hot-start polymerase at 95° C.; step 2), 10 seconds denaturation at 95° C.; step 3), 30 seconds primer annealing at 60° C. The cycle number of steps 2)+3) was 40. The 2(-delta delta C(T)) method (Livak K J, and Schmittgen T D: Analysis of relative gene expression data using real time quantitative PCR and the 2 (-delta delta C(T)) method. Methods 2001, 25: 402-408) was employed for the relative comparison of the gene expression.

The results of this study are shown in FIGS. 10 and 11 and demonstrate that *Cyanidium caldarium* extract is capable of significantly increasing the colony forming efficiency of epidermal progenitor cells during culturing. This means that *Cyanidium caldarium* extract maintains the stem cell character of the keratinocytes and that the cells do not enter the differentiation state. At the gene expression level it was observed that described stem cell marker genes in the progenitor keratinocytes were upregulated, which likewise suggests that the stem cell character of the keatinocytes can be stimulated during culturing by the addition of *Cyanidium caldarium* extract.

To summarize, Examples 4 to 7 demonstrate that *Cyanidium caldarium* extract is a potent cosmetic for strengthening skin elasticity by the synthesis of elastin and the surrounding extracellular dermal structures such as lumican and collagen. Moreover, *Cyanidium caldarium* extract, when applied to UV-stressed skin, results, by virtue of its anti-inflammatory activity, in the restitution of the epidermal homeostasis of the skin. Furthermore, *Cyanidium caldarium* extract maintains the stem cell functions in the epidermis, and therefore assists in maintaining three of the most important functions by way of protection against skin ageing.

Example 8

Improving the Mechanical Properties of Hair by Treatment with *Cyanidium Caldarium* Extract A piece of human natural European hair tresses, remis, double-drawn, with a length of 23 cm (21 cm freehair) and a width of 2.0 cm, with a weight of 2.0 g and a dark brown colour, was wetted within 10 seconds under a running tap. Thereafter, 8 g of a 30% strength aqueous hydrogen peroxide solution were mixed with 4 g of Basler Blond Claire bleaching powder, 2 ml of a 25% strength aqueous ammonia solution were added, everything was remixed, and 8 g of the resulting paste were massaged into the piece of tresses with the aid of a comb and the hands, which had been protected. After an exposure time of 30 minutes at room temperature, the piece of tresses was washed for 2 minutes under running tap water with a temperature of approximately 35° C. and then dried with an electronic hair dryer for 3 minutes with simultaneous combing. The entire procedure was repeated once, starting with the wetting of the piece of tresses. Thereafter, 40 hairs were removed from the piece of tresses, and in each case the middle part of one hair with a length of 3 cm was crimped between two brass sleeves with internal plastic coating. The mean area of each individual hair was measured by means of Dia-stron FDAS760 fibre dimensional analysis system and UvWin PC application software. Thereupon, the hair samples were transferred into the sample cartridge of a Dia-stron Tensile Tester MTT 670 and in each case treated with fully demineralised water which had been brought to pH 7 with citric acid. Measurement of the individual hair strands with the "single fibre method" (extension 20%, rate 20 mm/min, gauge force 2, maximum force 200, break threshold 5, sample size 30 mm) was started. Thereafter, the hair samples were removed from the sample cartridge and, in a small plastic dish, covered with fully demineralised water. After 30 minutes, the water was removed and the hair samples were covered with leave-on hair conditioner (Table 2).

TABLE 2

Test formulations. Data in percent by weight. Customary formulation known to the skilled worker were employed for preparing methods the formulations.

| | Raw material | Vehicle | 2.5% *Cyanidium caldarium* extract |
|---|---|---|---|
| A | TEGINACID C ® (ceteareth-25) | 0.5% | 0.5% |
| | TEGO Alkanol 1618 (cetearyl alcohol) | 2.0% | 2.0% |
| | *Cyanidium caldarium* extract | | 2.5% |
| | Water | to 100% | to 100% |
| | Methylchloroisothiazolinone, methyl isothiazolinone (Kathon ™ CG) | 0.05% | 0.05% |
| | Lactic acid (10% in water) | pH 4.0-4.5 | pH 4.0-4.5 |

After an exposure time of 30 minutes, each individual hair sample was washed for 6 seconds under the running water jet with a temperature of approximately 35° C. The hair samples were dried overnight at 22° C. and 50% relative atmospheric humidity. Thereafter, the measurement of the individual hair samples was repeated, starting with the transfer into the sample cartridge of the Dia-stron Tensile Tester MTT 670. The data are evaluated by means of a spreadsheet using the parameter modulus of elasticity (E module; FIG. 12). The E module describes the relationship between stress and elongation upon the deformation of a solid body at linear elastic behaviour ("Hooke's range"). Thus, the parameter E module represents the tensile strength of a hair fibre and has the unit $N/mm^2$.

As shown by the results of the tensile stress-elongation measurements, the addition of 2.5% *Cyanidium caldarium* extract to the leave-on hair conditioner caused an increase in the parameter E module by 25 $N/mm^2$. This demonstrated that the tensile strength of damaged hair is increased by *Cyanidium caldarium* extract.

Example 9

Enhancement of the Skin Elasticity and Improvement of the Skin Structure by *Cyanidium caldarium* Extract To demonstrate the enhancement of the skin elasticity and improvement of the skin structure by the topical application of *Cyanidium caldarium* extract, a human randomized vehicle-controlled blind application monitoring was performed over a period of eight weeks.

The panel comprised subjects aged 33-59 years (mean 47±8 years). Twenty subjects received vehicle formulation, 19 subjects the vehicle formulation comprising 1% *Cyanidium caldarium* extract and 21 subjects the vehicle formulation comprising 5% *Cyanidium caldarium* extract. The formulations were applied twice daily (in the morning and in the evening) to the inside of the forearm. 2 squeezes from a squeeze bottle (0.25-0.30 g) were applied by massaging in. The composition of the formulation is shown in Table 3:

TABLE 3

Test formulations. Data in Percent by weight. Customary formulation methods known to the skilled worker were employed for preparing the formulations.

| Raw material | Vehicle | 1% *Cyanidium* | 5% *Cyanidium* |
| --- | --- | --- | --- |
| TEGO ® Care 450 (polyglyceryl-3 methylglucose distearate) | 3.0 | 3.0 | 3.0 |
| TEGO ® Alkanol 18 (stearyl alcohol) | 0.5 | 0.5 | 0.5 |
| TEGIN ® M Pellets (glyceryl stearate) | 1.0 | 1.0 | 1.0 |
| TEGOSOFT ® CT (caprylic/capric triglycerides) | 6.0 | 6.0 | 6.0 |
| TEGOSOFT ® G 20 (octyldodecanol) | 2.0 | 2.0 | 2.0 |
| TEGOSOFT ® PC 41 (polyglyceryl-4 caprate) | 2.0 | 2.0 | 2.0 |
| Water | 85.2 | 84.2 | 80.2 |
| Xanthangum (Keltrol CG-SFT) | 0.3 | 0.3 | 0.3 |
| *Cyanidium caldarium* extract | | 1.0 | 5.0 |
| Methylisothiazolinone, ethylhexylglycerol (Euxyl K220) | 0.1 | 0.1 | 0.1 |
| pH (NaOH) | 5.5 | 5.5 | 5.5 |

The application phase extended over eight weeks. The parameters measured were the skin elasticity, using a Cutometer MPA 580 (Courage+Khazaka electronic GmbH) and the consistency of the skin surface, using Visioscan VC 98 (Courage+Khazaka electronic GmbH), on the inside of the forearm at the time T0 before the application phase and T8 after eight weeks. The data registered was the mean, which is calculated on the basis of the individual values of several repeated measurements. No formulation was applied on the evening before the respective measurement.

As demonstrated by the human in-vivo study, a reduction in the skin elasticity parameter R1 was observed over the period of eight weeks. R1 is the remaining deformation of the skin after the first extension cycle and represents the ability of the skin to return to its original state. The parameter R1 increases greatly with age. The reduction of R1 was approximately 5 mm in the group of persons who applied 1% *Cyanidium caldarium* extract, while the reduction in the group of persons who applied 5% *Cyanidium caldarium* extract was three times as pronounced (FIG. 13).

A similar trend was found for the skin elasticity parameter R4. R4 is the minimum amplitude of the last of the three extension cycles of the skin and visualizes "fatigue symptoms" of the skin since the redeformation ability is reduced with every additional extension (FIG. 14).

An increase in the skin texture parameter tex was also found. The parameter tex describes the uniformity of the skin tone. An improved tex value is associated with improved skin appearance. A pronounced increase of the tex parameter value by 30 and 24 units was found, after eight weeks, both in the 1% *Cyanidium* and in the 5% *Cyanidium* group, respectively (FIG. 15).

Finally, a reduction of the skin surface parameter and of the volume parameter was found. The skin surface parameter describes the total surface of the measured skin, while the volume parameter represents the volume required for filling the wrinkles in the skin. In the case of a reduction of the depth and number of wrinkles, the skin surface parameter and the volume parameter should decrease by 7 units was found in the 1% *Cyanidium* group while the 5% *Cyanidium* group showed a greater reduction of this value by 15 units (FIG. 16).

The results of the human in-vivo study demonstrate that the use of the cosmetic formulation according to the invention results in an enhanced skin elasticity and skin firmness, an improvement of the skin structure and a reduction of the depth and number of wrinkles.

Examples of Formulations

Example of an after-Shave Lotion Formulation

| Raw material | INCI | Percent by weight |
| --- | --- | --- |
| ABIL ® Care 85 | Bis-PEG/PPG-16/16 PEG/PPG16/16 dimethicone; caprylic/capric triglyceride | 1.5 |
| TEGOSOFT ® CT | Caprylic/capric triglyceride | 3.0 |
| Cyclomethicone | Cyclomethicone | 3.0 |
| Tocopheryl acetate | Tocopheryl acetate | 0.5 |
| Frescolate ML | Menthyl lactate, H&R | 0.5 |
| TEGO ® SMO 80 V | Polysorbate 80 | 0.5 |
| Water | Water | to 100 |
| *Cyanidium caldarium* extract | | 1.1 |
| Glycerol | | 2.0 |
| Ethanol | | 15.0 |
| TEGO ® Carbomer 141 | Carbomer | 0.3 |
| Xanthan gum | Xanthan gum | 0.1 |
| Mineral oil (30 mPas) | Mineral oil | 1.6 |
| Sodium hydroxide (10% in water) | | q.s. |
| Preservative, perfume | | q.s. |

Example of an O/W after-Shave Balm Formulation

| Raw material | INCI | Percent by weight |
| --- | --- | --- |
| AXOL ® C 62 pellets | Glyceryl stearate citrate | 1.50 |
| TEGO ® Alkanol 1618 | Cetearyl alcohol | 1.00 |
| TEGOSOFT ® CT | Caprylic/capric triglyceride | 5.00 |
| TEGOSOFT ® P | Isopropyl palmitate | 2.00 |

-continued

| Raw material | INCI | Percent by weight |
|---|---|---|
| Cyclomethicone | Cyclomethicone | 5.50 |
| Glycerol | Glycerol | 5.00 |
| *Cyanidium caldarium* extract | | 2.0 |
| Water | | to 100 |
| TEGO ® Carbomer 141 | Carbomer | 0.20 |
| TEGOSOFT ® P | Isopropyl palmitate | 0.80 |
| Sodium hydroxide (10% in water) | | q.s. |
| Preservative, perfume | | q.s. |

Example of a PEG- and Sulphate-Free Conditioning Shampoo Formulation

| Raw material | INCI | Percent by weight |
|---|---|---|
| REWOTERIC ® AM C | Sodium cocoamphoacetate | 15.0 |
| REWOPOL ® SB F 12 P | Disodium lauryl sulfosuccinate | 3.8 |
| Water | Water | to 100 |
| *Cyanidium caldarium* extract | | 0.5 |
| TEGO ® Betaine F 50 | Cocamidopropyl betaine | 10.0 |
| VARISOFT ® PATC | Palmitamidopropyltrimonium chloride | 2.3 |
| REWOMID ® SPA | Isostearamide MIPA | 1.0 |
| Citric acid | Citric acid | q.s. |
| Preservative, perfume | | q.s. |

Example of a Sprayable PEG-Free Hair Milk Formulation

| Raw material | INCI | Percent by weight |
|---|---|---|
| Lactic acid, 80% | Lactic acid | 0.40 |
| Water | Water | to 100 |
| *Cyanidium caldarium* extract | | 1.50 |
| TEGO ® Amid S 18 | Stearamidopropyl dimethylamine | 1.20 |
| TEGIN ® G 1100 pellets | Glycol distearate | 0.60 |
| TEGO ® Care PS | Methyl glucose sesquistearate | 1.20 |
| TEGOSOFT ® DEC | Diethylhexyl carbonate | 0.30 |
| Preservative, perfume | | q.s. |

Example of a Leave-in Conditioning Foam Formulation with Heat Protection Activity

| Raw material | INCI | Percent by weight |
|---|---|---|
| ABIL ® T Quat 60 | Silicone quaternium-22 | 0.5 |
| TAGAT ® CH 40 | PEG-40 hydrogenated castor oil | 0.5 |
| TEGO ® Betaine 810 | Capryl/capramidopropyl betaine | 2.0 |
| Water | Water | to 100 |
| *Cyanidium caldarium* extract | | 1.0 |
| TEGOCEL ® HPM 50 | Hydroxypropyl methylcellulose | 0.3 |
| VARISOFT ® 300 | Cetrimonium chloride | 1.3 |
| Citric acid, 30% | | q.s. |
| Preservative, perfume | | q.s. |

Example of a Sun Protective Caring Body Lotion Formulation

| Raw material | INCI | Percent by weight |
|---|---|---|
| TEGO ® Care 165 | Glyceryl stearate; PEG-100 stearate | 3.5 |
| TEGIN ® M pellets | Glyceryl stearate | 3.0 |
| TEGO ® Alkanol 18 | Stearyl alcohol | 2.0 |
| TEGOSOFT ® XC | Phenoxyethyl caprylate | 8.0 |
| Sylvaclear WF1500V | Polyamide-4, ArizonaChemical | 4.0 |
| TEGOSOFT ® APM | PPG-3 myristyl ether | 2.0 |
| Ethylhexyl methoxycinnamate | Ethylhexyl methoxycinnamate | 3.0 |
| Benzophenone-3 | Benzophenone-3 | 5.0 |
| Octocrylene | Octocrylene | 7.0 |
| Menthyl anthranilate | Menthyl anthranilate | 4.0 |
| TEGO ® Sun T 805 | Titanium dioxide; Trimethoxycaprylylsilane | 4.0 |
| Xanthan gum | Xanthan gum | 0.2 |
| Glycerol | Glycerol | 2.0 |
| Water | Water | to 100 |
| *Cyanidium caldarium* extract | | 1.0 |
| Allantoin | Allantoin | 0.1 |
| Tromethamin, 20% in water, Merck | Tris(hydroxymethyl)aminomethane | q.s. |
| Preservative, perfume | | q.s. |

Example of a Sun Care Soft Cream (Cold Processed) SPF 40+ Formulation

| Raw material | INCI | Percent by weight |
|---|---|---|
| ABIL ® Care XL 80 | Bis-PEG/PPG-20/5 PEG/PPG-20/5 dimethicone; methoxy PEG/PPG-25/4 dimethicone; caprylic/capric triglyceride | 2.5 |
| TEGO ® Sun TDEC 45 | Titanium dioxide; diethylhexyl carbonate; polyglyceryl-6 polyhydroxystearate | 11.0 |
| Ethylhexyl methoxycinnamate | | 8.0 |
| Octocrylene | | 7.5 |
| Butyl methoxydibenzoylmethane | | 3.0 |
| Tocopheryl acetate | | 0.5 |
| TEGO ® Carbomer 141 | Carbomer | 0.25 |
| TEGO ® Carbomer 341 ER | Acrylates/C10-30 alkyl acrylate crosspolymer | 0.25 |
| Xanthan gum | | 0.2 |
| TEGOSOFT ® P | Isopropyl palmitate | 2.0 |
| Water | Water | to 100 |
| Glycerol | | 3.0 |
| *Cyanidium caldarium* extract | | 1.0 |
| Sodium hydroxide (10% in water) | | q.s. |
| Preservative, perfume | | q.s. |

Example of an after-Sun Foam Formulation

| Raw material | INCI | Percent by weight |
|---|---|---|
| TEGINACID ® H | Glyceryl stearate; ceteth-20 | 3.60 |
| TEGO ® Alkanol 18 | Stearyl alcohol | 1.20 |
| TEGOSOFT ® CT | Caprylic/capric triglyceride | 3.60 |
| TEGOSOFT ® liquid | Cetearyl ethylhexanoate | 1.80 |
| TEGOSOFT ® P | Isopropyl palmitate | 1.80 |

-continued

| Raw material | INCI | Percent by weight |
|---|---|---|
| TEGOSOFT ® DO | Decyl oleate | 3.00 |
| Glycerol | | 1.80 |
| Panthenol | | 0.60 |
| Allantoin | | 0.10 |
| Water | Water | to 100 |
| *Cyanidium caldarium* extract | | 1.2 |
| TEGO ® Betaine 810 | Capryl/capramidopropyl betaine | 7.00 |
| Sodium hydroxide (10% in water) | | q.s. |
| Preservative, perfume | | q.s. |

Example of an O/W Cream Formulation

| Raw material | INCI | Percent by weight |
|---|---|---|
| TEGO ® Care PSC 3 | Polyglyceryl-3 dicitrate/stearate | 3.00 |
| TEGIN ® M pellets | Glyceryl stearate | 1.20 |
| TEGO ® Alkanol 18 | Stearyl alcohol | 0.80 |
| TEGOSOFT ® P | Isopropyl palmitate | 7.00 |
| *Prunus amygdalus dulcis* oil | | 5.00 |
| TEGOSOFT ® CT | Caprylic/capric triglyceride | 4.50 |
| TEGOSOFT ® TIS | Triisostearin | 3.50 |
| Water | Water | to 100 |
| *Cyanidium caldarium* extract | | 2.0 |
| Glycerol | | 3.00 |
| Keltrol CG-SFT, CP Kelco | Xanthan gum | 0.30 |
| Sodium hydroxide (10% in water) | | q.s. |
| Preservative, perfume | | q.s. |

Example of an Anti-Cellulite Body Lotion Formulation

| Raw material | INCI | Percent by weight |
|---|---|---|
| TEGO ® Care LTP | Sorbitan laurate; polyglyceryl-4 laurate; dilauryl citrate | 1.50 |
| TEGOSOFT ® CI | Cetearyl isononanoate | 10.00 |
| TEGOSOFT ® DEC | Diethylhexyl carbonate | 3.50 |
| TEGOSOFT ® OP | Ethylhexyl palmitate | 1.10 |
| TEGO ® Carbomer 140 | Carbomer | 0.15 |
| TEGO ® Carbomer 141 | Carbomer | 0.15 |
| Xanthan gum | | 0.10 |
| Glycerol | | 3.00 |
| Water | Water | to 100 |
| *Cyanidium caldarium* extract | | 3.0 |
| Sodium hydroxide (10% in water) | | q.s. |
| Preservative, perfume | | q.s. |

Example of a Moisturizing Anti-Cellulite Cream Gel Formulation

| Raw material | INCI | Percent by weight |
|---|---|---|
| TEGOSOFT ® DC | Decyl cocoate | 8.00 |
| TEGOSOFT ® OP | Ethylhexyl palmitate | 5.00 |
| TEGOSOFT ® CR | Cetyl ricinoleate | 2.00 |
| TEGO ® Alkanol 1618 | Cetearyl alcohol | 1.00 |
| Tocopheryl acetate | | 0.50 |

-continued

| Raw material | INCI | Percent by weight |
|---|---|---|
| TEGOSOFT ® PSE 141 G | Sucrose stearate | 2.00 |
| TEGO ® Care CG 90 | Cetearyl glucoside | 0.50 |
| Glycerol | | 4.00 |
| Panthenol | | 0.50 |
| Water | Water | to 100 |
| *Cyanidium caldarium* extract | | 5.6 |
| TEGO ® Carbomer 341 ER | Acrylates/C10-30 alkyl acrylate crosspolymer | 0.45 |
| Sodium hydroxide (10% in water) | | q.s. |
| Preservative, perfume | | q.s. |

Example of a New-Generation Anti-Ageing Moisturizer Formulation

| Raw material | INCI | Percent by weight |
|---|---|---|
| TEGO ® Care 450 | Polyglyceryl-3 methylglucose distearate | 3.00 |
| TEGIN ® M pellets | Glyceryl stearate | 2.50 |
| TEGO ® Alkanol 18 | Stearyl alcohol | 1.50 |
| TEGOSOFT ® MM | Myristyl myristate | 1.00 |
| TEGOSOFT ® DO | Decyl oleate | 8.00 |
| TEGOSOFT ® OS | Ethylhexyl stearate | 9.00 |
| Phytosphingosine SLC | Salicyloyl phytosphingosine | 0.10 |
| Glycerol | | 3.00 |
| Water | Water | to 100 |
| *Cyanidium caldarium* extract | | 5.0 |
| TEGO ® Carbomer 134 | Carbomer | 0.20 |
| TEGOSOFT ® P | Isopropyl palmitate | 0.80 |
| Sodium hydroxide (10% in water) | | q.s. |
| Preservative, perfume | | q.s. |

Example of a W/O Lotion Formulation

| Raw material | INCI | Percent by weight |
|---|---|---|
| ISOLAN ® GPS | Polyglyceryl-4 diisostearate/polyhydroxystearate/sebacate | 3.0 |
| Paracera W 80, Paramelt B.V. | Microcrystalline wax | 0.1 |
| Hydrogenated castor oil | | 0.1 |
| TEGOSOFT ® DEC | Diethylhexyl carbonate | 7.0 |
| TEGOSOFT ® TIS | Triisostearin | 3.0 |
| Cyclomethicone | | 7.0 |
| Glycerol | | 3.0 |
| Magnesium sulphate heptahydrate | | 1.0 |
| TEGO ® Cosmo C 100 | Creatine | 1.0 |
| Skinmimics ® | Ceteareth-25; glycerol; cetyl alcohol; behenic acid; cholesterol; ceramide NP; ceramide NS; ceramide EOS; ceramide EOP; ceramide AP; caprooyl phytosphingosine; caprooyl sphingosine | 5.0 |
| Water | Water | to 100 |
| *Cyanidium caldarium* extract | | 4.5 |
| Preservative, perfume | | q.s. |

Example of a Winter Skin Moisturizer Formulation

| Raw material | INCI | Percent by weight |
|---|---|---|
| ABIL ® EM 90 | Cetyl PEG/PPG-10/1 dimethicone | 2.0 |
| Hydrogenated castor oil | | 0.5 |
| Paracera W 80, Paramelt B.V. | Microcrystalline wax | 0.5 |
| TEGOSOFT ® CT | Caprylic/Capric triglyceride | 10.0 |
| TEGOSOFT ® HP | Isocetyl palmitate | 10.0 |
| TEGOSOFT ® DEC | Diethylhexyl carbonate | 5.0 |
| Water | Water | to 100 |
| Sodium chloride | Sodium chloride | 0.5 |
| *Cyanidium caldarium* extract | | 15 |
| Preservative, perfume | | q.s. |

The invention claimed is:

1. A process for the production of 4-aminobutyric acid, comprising: culturing *Cyanidium caldarium* cells containing 4-aminobutyric acid in an aqueous medium; disrupting the *Cyanidium caldarium* cells to obtain solid cell components containing said 4-aminobutyric acid; and incorporating the disrupted *Cyanidium caldarium* cells comprising solid cell components containing said 4-aminobutyric acid in a cosmetic formulation.

2. The process according to claim 1, wherein said *Cyanidium caldarium* cells are cultured at a temperature from 20° C. to 60° C.

3. The process according to claim 1, wherein said culturing provides an aqueous medium having a pH at 25° C. of from 1.5 to 6.

4. The process according claim 1, wherein said disrupting the *Cyanidium caldarium* cells is performed in an aqueous medium.

5. The process according to claim 1, wherein said disrupting the *Cyanidium caldarium* cells comprises a hot-water disruption in combination with an enzymatic cell disruption.

* * * * *

SEQUENCE LISTING

<160> NUMBER OF SEQ ID NOS: 42

<210> SEQ ID NO 1
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 1
gcctcggagg aaactttg                          18

<210> SEQ ID NO 2
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 2
gacccatggg acctgaag                          18

<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 3
gcccagtttg gcctagtg                          18

<210> SEQ ID NO 4
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 4
cagcagcacc gtatttag                          18

<210> SEQ ID NO 5
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 5
tgggagcaaa cacatctga                         19

<210> SEQ ID NO 6

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
atcacttctc cccgaatcgt                                               20

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
tcgcccggca gcaaactcag                                               20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
tcacaccgct cacaggggct                                               20

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
caggctagag aagcagagcc                                               20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
tggagatttt gggagtacgg                                               20

<210> SEQ ID NO 11
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 11
cgtggatcct gctcacct                                                 18

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
```
caatggagct gttgtcaagg                                              20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
ggttgagctg gatctgtcct                                              20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
agtaggataa tggccccagg                                              20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
accacagtcc atgccatcac                                              20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
tccaccaccc tgttgctgta                                              20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
cctggatgac tcttgggaaa                                              20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
tcagccagct gtttcatgtc                                              20

<210> SEQ ID NO 19
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 19
ctctggccca ggcagtcaga                                               20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
ggcgtttggg aaggttggat                                               20

<210> SEQ ID NO 21
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 21
cactccatga aggctgcatg g                                             21

<210> SEQ ID NO 22
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 22
acccagtagt cttgctttgt gg                                            22

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
accacagtcc atgccatcac                                               20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
tccaccaccc tgttgctgta                                               20

<210> SEQ ID NO 25
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 25
ccaccagagc tattcccaaa ag                                            22
```

```
<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
gcggcgattc atcaggaaat                                               20

<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 27
tgccaagtgg gtggtataga                                               20

<210> SEQ ID NO 28
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 28
tcagatgacg aagagcacag a                                             21

<210> SEQ ID NO 29
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 29
atgtgaatgc caaagcgaag                                               20

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 30
ctaccaacac gcccttcatt                                               20

<210> SEQ ID NO 31
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 31
ctcttcggct tctcgctg                                                 18

<210> SEQ ID NO 32
<211> LENGTH: 19
<212> TYPE: DNA
<213> ORGANISM: Artificial Sequence
<220> FEATURE:
```

<223> OTHER INFORMATION: synthetic oligonucleotide

<400> SEQUENCE: 32
cccgttctgt tggctctct                                                    19

<210> SEQ ID NO 33
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 33
gacctgccct cctggac                                                      17

<210> SEQ ID NO 34
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 34
gtaggttcgg caagtcctca                                                   20

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
cggcctgctg ctccttggtc                                                   20

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
caccgctgtg cctctggcat                                                   20

<210> SEQ ID NO 37
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 37
atcgtcccag gtggaagagt t                                                 21

<210> SEQ ID NO 38
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 38
atagtaacca ggcgtctcgt gg                                                22

```
<210> SEQ ID NO 39
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 39
ggcctgctga gatcaaagac                                              20

<210> SEQ ID NO 40
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 40
tctgcagaag gacattggc                                               19

<210> SEQ ID NO 41
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 41
gtgctcgcgc tactctctct                                              20

<210> SEQ ID NO 42
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 42
ttcaatgtcg gatggatgaa                                              20
```